Figure 1:
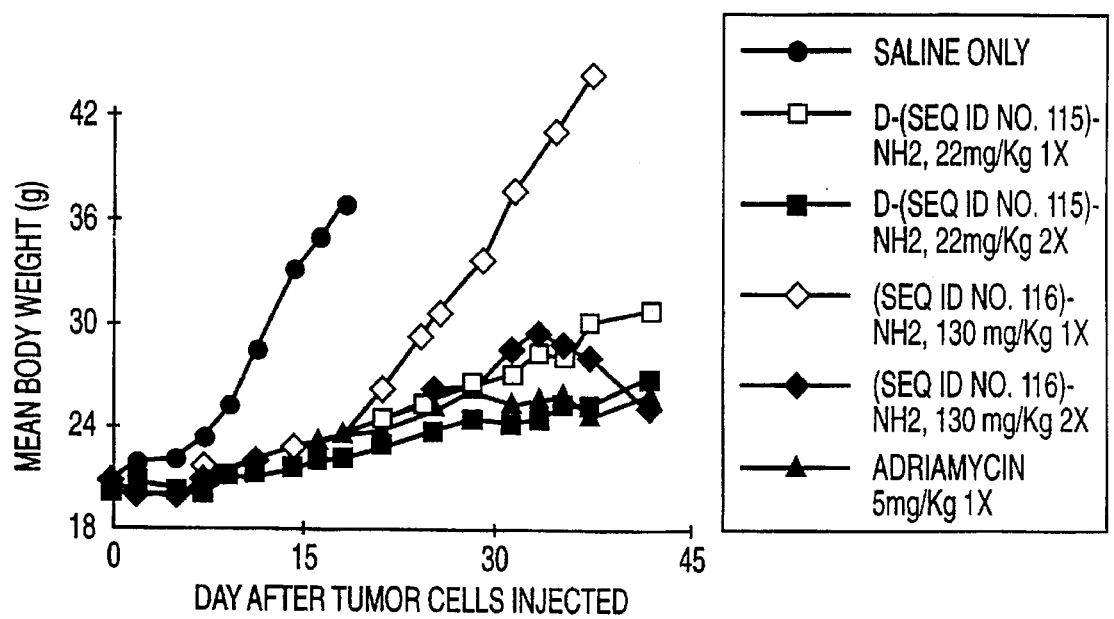

US005635479A

United States Patent [19]
Jacob et al.

[11] Patent Number: 5,635,479
[45] Date of Patent: Jun. 3, 1997

[54] TREATMENT OF GYNECOLOGICAL MALIGNANCIES WITH BIOLOGICALLY ACTIVE PEPTIDES

[75] Inventors: Leonard S. Jacob, Penn Valley; W. Lee Maloy, Lansdale; Margaret A. Baker, Philadelphia, all of Pa.

[73] Assignee: Magainin Pharmaceuticals Inc., Plymouth Meeting, Pa.

[21] Appl. No.: 434,120

[22] Filed: May 2, 1995

Related U.S. Application Data

[63] Continuation of Ser. No. 297,950, Aug. 31, 1994, abandoned, which is a continuation of Ser. No. 226,108, Apr. 11, 1994, abandoned, which is a continuation of Ser. No. 937,462, Aug. 31, 1992, abandoned.

[51] Int. Cl.⁶ ............................ A61K 36/00; C07K 14/00
[52] U.S. Cl. .................................... 514/12; 514/21
[58] Field of Search ............................ 514/12, 21

[56] References Cited

U.S. PATENT DOCUMENTS

| | | | |
|---|---|---|---|
| 4,810,777 | 3/1989 | Zasloff | 530/326 |
| 4,962,277 | 10/1990 | Cuervo et al. | 514/14 |
| 5,073,542 | 12/1991 | Zasloff | 514/12 |

OTHER PUBLICATIONS

Ozols et al., Kinetic Characterization and Response to Chemotherapy in a Transplantable Murine Ovarian Cancer, Cancer Research, vol. 39, No. 8, CNREAB 8, pp. 2909–3288 (1979).

Cecil's Textbook of Medicine, ed. Wyngaarden, Smith, Jr. and Bennett, pp. 1395–1397 (19th Edition).

Baker et al., "Anticancer Efficacy of Magainin2 and Analogue Peptides," Cancer Research, vol. 53, pp. 3052–43057, (Jul. 1, 1993).

Primary Examiner—Howard E. Schain
Assistant Examiner—P. L. Touzeau
Attorney, Agent, or Firm—Finnegan, Henderson, Farabow, Garrett & Dunner, L.L.P.

[57] ABSTRACT

A process for treating a gynecological malignancy in a host which comprises administering to the host at least one biologically active amphiphilic peptide or protein. The peptide or protein may be administered intralesionally, intravenously, or intraperitoneally, whereby the peptide or protein may inhibit, prevent, or destroy the growth of the gynecological malignancy, such as an ovarian cancer, uterine cancer, or cervical cancer.

6 Claims, 2 Drawing Sheets

SEQUENCE LISTING ( 1 ) GENERAL INFORMATION:

( i i i ) NUMBER OF SEQUENCES: 117

( 2 ) INFORMATION FOR SEQ ID NO:1:

( i ) SEQUENCE CHARACTERISTICS:
       ( A ) LENGTH: 20 amino acids
       ( B ) TYPE: amino acid
       ( C ) STRANDEDNESS:
       ( D ) TOPOLOGY: linear ( i i ) MOLECULE TYPE: peptide ( x ) PUBLICATION INFORMATION:
       ( H ) DOCUMENT NUMBER: WO89/11290
       ( I ) FILING DATE: 19-MAY-1989
       ( J ) PUBLICATION DATE: 30-NOV-1989

( x i ) SEQUENCE DESCRIPTION: SEQ ID NO:1:

```
Ala  Phe  Ser  Lys  Ala  Phe  Ser  Lys  Ala  Phe
                      5                         10
Ser  Lys  Ala  Phe  Ser  Lys  Ala  Phe  Ser  Lys
                     15                         20
```

( 2 ) INFORMATION FOR SEQ ID NO:2:

( i ) SEQUENCE CHARACTERISTICS:
       ( A ) LENGTH: 24 amino acids
       ( B ) TYPE: amino acid
       ( C ) STRANDEDNESS:
       ( D ) TOPOLOGY: linear (ii) MOLECULE TYPE: peptide (x) PUBLICATION INFORMATION:
    (H) DOCUMENT NUMBER: WO89/11290
    (I) FILING DATE: 19-MAY-1989
    (J) PUBLICATION DATE: 30-NOV-1989

(xi) SEQUENCE DESCRIPTION: SEQ ID NO:2:

```
Ala  Phe  Ser  Lys  Ala  Phe  Ser  Lys  Ala  Phe
                    5                         10

Ser  Lys  Ala  Phe  Ser  Lys  Ala  Phe  Ser  Lys
                    15                        20

Ala  Phe  Ser  Lys
```

(2) INFORMATION FOR SEQ ID NO:3:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (x) PUBLICATION INFORMATION:
    (H) DOCUMENT NUMBER: WO89/11290
    (I) FILING DATE: 19-MAY-1989
    (J) PUBLICATION DATE: 30-NOV-1989

(xi) SEQUENCE DESCRIPTION: SEQ ID NO:3:

```
Phe  Ser  Lys  Ala  Phe  Ser  Lys  Ala  Phe  Ser
                    5                         10

Lys  Ala  Phe  Ser  Lys  Ala
                    15
```

(2) INFORMATION FOR SEQ ID NO:4:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (x) PUBLICATION INFORMATION:
    (H) DOCUMENT NUMBER: WO89/11290
    (I) FILING DATE: 19-MAY-1989
    (J) PUBLICATION DATE: 30-NOV-1989

(xi) SEQUENCE DESCRIPTION: SEQ ID NO:4:

```
Ser  Lys  Ala  Phe  Ser  Lys  Ala  Phe  Ser  Lys
                    5                         10

Ala  Phe  Ser  Lys  Ala  Phe  Ser  Lys  Ala  Phe
                    15                        20
```

(2) INFORMATION FOR SEQ ID NO:5:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (x) PUBLICATION INFORMATION:
    (H) DOCUMENT NUMBER: WO89/11290
    (I) FILING DATE: 19-MAY-1989
    (J) PUBLICATION DATE: 30-NOV-1989

( x i ) SEQUENCE DESCRIPTION: SEQ ID NO:5:

Lys Ala Phe Ser Lys Ala Phe Ser Lys Ala
                    5                       10

Phe Ser Lys Ala Phe Ser
                15

( 2 ) INFORMATION FOR SEQ ID NO:6:

( i ) SEQUENCE CHARACTERISTICS:
        ( A ) LENGTH: 23 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Magainin I peptide.

( x ) PUBLICATION INFORMATION:
        ( A ) AUTHORS: Zasloff, Michael
        ( C ) JOURNAL: Proc. Nat. Acad. Sci.
        ( D ) VOLUME: 84
        ( F ) PAGES: 5449-5453
        ( G ) DATE: AUG - 1987
        ( H ) DOCUMENT NUMBER: US 4810777
        ( I ) FILING DATE: 04-MAR-1987
        ( J ) PUBLICATION DATE: 07-MAR- 1989

( x i ) SEQUENCE DESCRIPTION: SEQ ID NO:6:

Gly Ile Gly Lys Phe Leu His Ser Ala Gly
                    5                       10

Lys Phe Gly Lys Ala Phe Val Gly Glu Ile
                15                      20

Met Lys Ser ( 2 ) INFORMATION FOR SEQ ID NO:7:

( i ) SEQUENCE CHARACTERISTICS:
        ( A ) LENGTH: 23 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Magainin II peptide.

( x ) PUBLICATION INFORMATION:
        ( A ) AUTHORS: Zasloff, Michael
        ( C ) JOURNAL: Proc. Nat. Acad. Sci.
        ( D ) VOLUME: 84
        ( F ) PAGES: 5449-5453
        ( G ) DATE: AUG - 1987
        ( H ) DOCUMENT NUMBER: US 4810777
        ( I ) FILING DATE: 04-MAR-1987
        ( J ) PUBLICATION DATE: 07-MAR- 1989

( x i ) SEQUENCE DESCRIPTION: SEQ ID NO:7:

Gly Ile Gly Lys Phe Leu His Ser Ala Lys
                    5                       10

Lys Phe Gly Lys Ala Phe Val Gly Glu Ile
                15                      20

Met Asn Ser ( 2 ) INFORMATION FOR SEQ ID NO:8:

( i ) SEQUENCE CHARACTERISTICS:
                ( A ) LENGTH: 22 amino acids
                ( B ) TYPE: amino acid
                ( C ) STRANDEDNESS:
                ( D ) TOPOLOGY: linear ( i i ) MOLECULE TYPE: peptide ( i x ) FEATURE:
                ( A ) NAME/KEY: Magainin III peptide.

( x ) PUBLICATION INFORMATION:
                ( A ) AUTHORS: Zasloff, Michael
                ( C ) JOURNAL: Proc. Nat. Acad. Sci.
                ( D ) VOLUME: 84
                ( F ) PAGES: 5449-5453
                ( G ) DATE: AUG - 1987
                ( H ) DOCUMENT NUMBER: US 4810777
                ( I ) FILING DATE: 04-MAR-1987
                ( J ) PUBLICATION DATE: 07-MAR- 1989

( x i ) SEQUENCE DESCRIPTION: SEQ ID NO:8:

| Gly | Ile | Gly | Lys | Phe | Leu | His | Ser | Ala | Lys |
|-----|-----|-----|-----|-----|-----|-----|-----|-----|-----|
|     |     |     |     | 5   |     |     |     |     | 10  |
| Lys | Phe | Gly | Lys | Ala | Phe | Val | Gly | Glu | Ile |
|     |     |     |     | 15  |     |     |     |     | 20  |
| Met | Asn |     |     |     |     |     |     |     |     |

( 2 ) INFORMATION FOR SEQ ID NO:9:

( i ) SEQUENCE CHARACTERISTICS:
                ( A ) LENGTH: 22 amino acids
                ( B ) TYPE: amino acid
                ( C ) STRANDEDNESS:
                ( D ) TOPOLOGY: linear ( i i ) MOLECULE TYPE: peptide ( i x ) FEATURE:
                ( A ) NAME/KEY: magainin peptide.

( x ) PUBLICATION INFORMATION:
                ( A ) AUTHORS: Zasloff, Michael
                ( C ) JOURNAL: Proc. Nat. Acad. Sci.
                ( D ) VOLUME: 84
                ( F ) PAGES: 5449-5453
                ( G ) DATE: AUG - 1987
                ( H ) DOCUMENT NUMBER: US 4810777
                ( I ) FILING DATE: 04-MAR-1987
                ( J ) PUBLICATION DATE: 07-MAR- 1989

( x i ) SEQUENCE DESCRIPTION: SEQ ID NO:9:

| Ile | Gly | Lys | Phe | Leu | His | Ser | Ala | Lys | Lys |
|-----|-----|-----|-----|-----|-----|-----|-----|-----|-----|
|     |     |     |     | 5   |     |     |     |     | 10  |
| Phe | Gly | Lys | Ala | Phe | Val | Gly | Glu | Ile | Met |
|     |     |     |     | 15  |     |     |     |     | 20  |
| Asn | Ser |     |     |     |     |     |     |     |     |

( 2 ) INFORMATION FOR SEQ ID NO:10:

( i ) SEQUENCE CHARACTERISTICS:
                ( A ) LENGTH: 21 amino acids
                ( B ) TYPE: amino acid
                ( C ) STRANDEDNESS:
                ( D ) TOPOLOGY: linear ( i i ) MOLECULE TYPE: peptide ( i x ) FEATURE:
                ( A ) NAME/KEY: magainin peptide.

( x ) PUBLICATION INFORMATION:

(A) AUTHORS: Zasloff, Michael
(C) JOURNAL: Proc. Nat. Acad. Sci.
(D) VOLUME: 84
(F) PAGES: 5449-5453
(G) DATE: AUG - 1987
(H) DOCUMENT NUMBER: US 4810777
(I) FILING DATE: 04-MAR-1987
(J) PUBLICATION DATE: 07-MAR- 1989

(xi) SEQUENCE DESCRIPTION: SEQ ID NO:10:

Gly Lys Phe Leu His Ser Ala Lys Lys Phe
                  5                   10

Gly Lys Ala Phe Val Gly Glu Ile Met Asn
                 15                   20

Ser (2) INFORMATION FOR SEQ ID NO:11:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: magainin peptide.

(x) PUBLICATION INFORMATION:
        (A) AUTHORS: Zasloff, Michael
        (C) JOURNAL: Proc. Nat. Acad. Sci.
        (D) VOLUME: 84
        (F) PAGES: 5449-5453
        (G) DATE: AUG - 1987
        (H) DOCUMENT NUMBER: US 4810777
        (I) FILING DATE: 04-MAR-1987
        (J) PUBLICATION DATE: 07-MAR- 1989

(xi) SEQUENCE DESCRIPTION: SEQ ID NO:11:

Lys Phe Leu His Ser Ala Lys Lys Phe Gly
                  5                   10

Lys Ala Phe Val Gly Glu Ile Met Asn Ser
                 15                   20

(2) INFORMATION FOR SEQ ID NO:12:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: PGLa peptide.

(x) PUBLICATION INFORMATION:
        (A) AUTHORS: Hoffman, et al.
        (C) JOURNAL: EMBO J.
        (D) VOLUME: 2
        (F) PAGES: 711-714
        (G) DATE: 1983
        (A) AUTHORS: Andreu, et al.
        (C) JOURNAL: Journal of Biochemistry
        (D) VOLUME: 149
        (F) PAGES: 531-535
        (G) DATE: 1985
        (A) AUTHORS: Gibson, et al.
        (C) JOURNAL: J. Biol. Chem.
        (D) VOLUME: 261
        (F) PAGES: 5341-5349

( G ) DATE: 1986
( A ) AUTHORS: Giovannini, et al.
( C ) JOURNAL: Biochem J.
( D ) VOLUME: 243
( F ) PAGES: 113-120
( G ) DATE: 1987

( x i ) SEQUENCE DESCRIPTION: SEQ ID NO:12:

Gly Met Ala Ser Lys Ala Gly Ala Ile Ala
                 5                   10

Gly Lys Ile Ala Lys Val Ala Leu Lys Ala
                15                   20

Leu ( 2 ) INFORMATION FOR SEQ ID NO:13:

( i ) SEQUENCE CHARACTERISTICS:
( A ) LENGTH: 25 amino acids
( B ) TYPE: amino acid
( C ) STRANDEDNESS:
( D ) TOPOLOGY: linear ( i i ) MOLECULE TYPE: peptide ( i x ) FEATURE:
( A ) NAME/KEY: XPF peptide.

( x ) PUBLICATION INFORMATION:
( A ) AUTHORS: Hoffman, et al.1
( C ) JOURNAL: EMBO J.
( D ) VOLUME: 2
( F ) PAGES: 711-714
( G ) DATE: 1983
( A ) AUTHORS: Andreu, et al.
( C ) JOURNAL: Journal of Biochemistry
( D ) VOLUME: 149
( F ) PAGES: 531-535
( G ) DATE: 1985
( A ) AUTHORS: Gibson, et al.
( C ) JOURNAL: J. Biol. Chem.
( D ) VOLUME: 261
( F ) PAGES: 5341-5349
( G ) DATE: 1986
( A ) AUTHORS: Giovannini, et al.
( C ) JOURNAL: Biochem J.
( D ) VOLUME: 243
( F ) PAGES: 113-120
( G ) DATE: 1987

( x i ) SEQUENCE DESCRIPTION: SEQ ID NO:13:

Gly Trp Ala Ser Lys Ile Gly Gln Thr Leu
                 5                   10

Gly Lys Ile Ala Lys Val Gly Leu Lys Glu
                15                   20

Leu Ile Gln Pro Lys
              25

( 2 ) INFORMATION FOR SEQ ID NO:14:

( i ) SEQUENCE CHARACTERISTICS:
( A ) LENGTH: 27 amino acids
( B ) TYPE: amino acid
( C ) STRANDEDNESS:
( D ) TOPOLOGY: linear ( i i ) MOLECULE TYPE: peptide ( i x ) FEATURE:
( A ) NAME/KEY: CPF peptide.

( x ) PUBLICATION INFORMATION:
( A ) AUTHORS: Richter, K.

Egger, R.
Kreil
(C) JOURNAL: J. Biol. Chem.
(D) VOLUME: 261
(F) PAGES: 3676-3680
(G) DATE: 1986
(A) AUTHORS: Wakabayashi, T.
Kato, H.
Tachibaba, S.
(C) JOURNAL: Nucleic Acids Research
(D) VOLUME: 13
(F) PAGES: 1817-1828
(G) DATE: 1985
(A) AUTHORS: Gibson, B.W.
Poulter, L.
Williams, D.H.
Maggio, J.E.
(C) JOURNAL: J. Biol. Chem.
(D) VOLUME: 261
(F) PAGES: 5341-5349
(G) DATE: 1986
(H) DOCUMENT NUMBER: WO90/04407
(I) FILING DATE: 16-OCT-1989
(J) PUBLICATION DATE: 03-MAY-1990

(xi) SEQUENCE DESCRIPTION: SEQ ID NO:14:

Gly Phe Gly Ser Phe Leu Gly Leu Ala Leu
                 5                   10
Lys Ala Ala Leu Lys Ile Gly Ala Asn Ala
                15                   20
Leu Gly Gly Ala Pro Gln Gln
                25

(2) INFORMATION FOR SEQ ID NO:15:

(i) SEQUENCE CHARACTERISTICS:
(A) LENGTH: 27 amino acids
(B) TYPE: amino acid
(C) STRANDEDNESS:
(D) TOPOLOGY: linear (ii) MOLECULE TYPE: peptide (ix) FEATURE:
(A) NAME/KEY: CPF peptide.

(x) PUBLICATION INFORMATION:
(A) AUTHORS: Richter, K
Egger, R.
Kreil
(C) JOURNAL: J. Biol. Chem.
(D) VOLUME: 261
(F) PAGES: 3676-3680
(G) DATE: 1986
(A) AUTHORS: Wakabayashi, T.
Kato, H.
Tachibaba, S.
(C) JOURNAL: Nucleic Acids Research
(D) VOLUME: 13
(F) PAGES: 1817-1828
(G) DATE: 1985
(A) AUTHORS: Gibson, B.W.
Poulter, L.
Williams, D.H.
Maggio, J.E.
(C) JOURNAL: J. Biol. Chem.
(D) VOLUME: 261
(F) PAGES: 5341-5349
(G) DATE: 1986
(H) DOCUMENT NUMBER: WO90/04407
(I) FILING DATE: 16-OCT-1989
(J) PUBLICATION DATE: 03-MAY-1990

(xi) SEQUENCE DESCRIPTION: SEQ ID NO:15:

```
Gly Leu Ala Ser Phe Leu Gly Lys Ala Leu
                 5                   10

Lys Ala Gly Leu Lys Ile Gly Ala His Leu
                 15                  20

Leu Gly Gly Ala Pro Gln Gln
                 25
```

( 2 ) INFORMATION FOR SEQ ID NO:16:

( i ) SEQUENCE CHARACTERISTICS:
        ( A ) LENGTH: 27 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: CPF peptide.

( x ) PUBLICATION INFORMATION:
        ( A ) AUTHORS: Richter, K.
              Egger, R.
              Kreil
        ( C ) JOURNAL: J. Biol. Chem.
        ( D ) VOLUME: 261
        ( F ) PAGES: 3676-3680
        ( G ) DATE: 1986
        ( A ) AUTHORS: Wakabayashi, T.
              Kato, H.
              Tachibaba, S.
        ( C ) JOURNAL: Nucleic Acids Research
        ( D ) VOLUME: 13
        ( F ) PAGES: 1817-1828
        ( G ) DATE: 1985
        ( A ) AUTHORS: Gibson, B.W.
              Poulter, L.
              Williams, D.H.
              Maggio, J.E.
        ( C ) JOURNAL: J. Biol. Chem.
        ( D ) VOLUME: 261
        ( F ) PAGES: 5341-5349
        ( G ) DATE: 1986
        ( H ) DOCUMENT NUMBER: WO90/04407
        ( I ) FILING DATE: 16-OCT-1989
        ( J ) PUBLICATION DATE: 03-MAY-1990

( x i ) SEQUENCE DESCRIPTION: SEQ ID NO:16:

```
Gly Leu Ala Ser Leu Leu Gly Lys Ala Leu
                 5                   10

Lys Ala Gly Leu Lys Ile Gly Thr His Phe
                 15                  20

Leu Gly Gly Ala Pro Gln Gln
                 25
```

( 2 ) INFORMATION FOR SEQ ID NO:17:

( i ) SEQUENCE CHARACTERISTICS:
        ( A ) LENGTH: 27 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: CPF peptide.

( x ) PUBLICATION INFORMATION:
        ( A ) AUTHORS: Richter, K.
              Egger, R.
              Kreil
        ( C ) JOURNAL: J. Biol. Chem.

(D) VOLUME: 261
(F) PAGES: 3676-3680
(G) DATE: 1986
(A) AUTHORS: Wakabayashi, T.
　　　　　　　Kato, H.
　　　　　　　Tachibaba, S.
(C) JOURNAL: Nucleic Acids Research
(D) VOLUME: 13
(F) PAGES: 1817-1828
(G) DATE: 1985
(A) AUTHORS: Gibson, B.W.
　　　　　　　Poulter, L.
　　　　　　　Williams, D.H.
　　　　　　　Maggio, J.E.
(C) JOURNAL: J. Biol. Chem.
(D) VOLUME: 261
(F) PAGES: 5341-5349
(G) DATE: 1986
(H) DOCUMENT NUMBER: WO90/04407
(I) FILING DATE: 16-OCT-1989
(J) PUBLICATION DATE: 03-MAY-1990

(xi) SEQUENCE DESCRIPTION: SEQ ID NO:17:

```
Gly Leu Ala Ser Leu Leu Gly Lys Ala Leu
                 5                      10
Lys Ala Thr Leu Lys Ile Gly Thr His Phe
                15                      20
Leu Gly Gly Ala Pro Gln Gln
                25
```

(2) INFORMATION FOR SEQ ID NO:18:

(i) SEQUENCE CHARACTERISTICS:
　　　　(A) LENGTH: 27 amino acids
　　　　(B) TYPE: amino acid
　　　　(C) STRANDEDNESS:
　　　　(D) TOPOLOGY: linear (ii) MOLECULE TYPE: peptide (ix) FEATURE:
　　　　(A) NAME/KEY: CPF peptide.

(x) PUBLICATION INFORMATION:
　　　　(A) AUTHORS: Richter, K.
　　　　　　　　　　　Egger, R.
　　　　　　　　　　　Kreil
　　　　(C) JOURNAL: J. Biol. Chem.
　　　　(D) VOLUME: 261
　　　　(F) PAGES: 3676-3680
　　　　(G) DATE: 1986
　　　　(A) AUTHORS: Wakabayashi, T.
　　　　　　　　　　　Kato, H.
　　　　　　　　　　　Tachibaba, S.
　　　　(C) JOURNAL: Nucleic Acids Research
　　　　(D) VOLUME: 13
　　　　(F) PAGES: 1817-1828
　　　　(G) DATE: 1985
　　　　(A) AUTHORS: Gibson, B.W.
　　　　　　　　　　　Poulter, L.
　　　　　　　　　　　Williams, D.H.
　　　　　　　　　　　Maggio, J.E.
　　　　(C) JOURNAL: J. Biol. Chem.
　　　　(D) VOLUME: 261
　　　　(F) PAGES: 5341-5349
　　　　(G) DATE: 1986
　　　　(H) DOCUMENT NUMBER: WO90/04407
　　　　(I) FILING DATE: 16-OCT-1989
　　　　(J) PUBLICATION DATE: 03-MAY-1990

(xi) SEQUENCE DESCRIPTION: SEQ ID NO:18:

```
Gly  Phe  Ala  Ser  Phe  Leu  Gly  Lys  Ala  Leu
                5                          10

Lys  Ala  Ala  Leu  Lys  Ile  Gly  Ala  Asn  Met
                15                         20

Leu  Gly  Gly  Thr  Pro  Gln  Gln
                25
```

( 2 ) INFORMATION FOR SEQ ID NO:19:

( i ) SEQUENCE CHARACTERISTICS:
        ( A ) LENGTH: 27 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: CPF peptide.

( x ) PUBLICATION INFORMATION:
        ( A ) AUTHORS: Richter, K.
                Egger, R.
                Kreil
        ( C ) JOURNAL: J. Biol. Chem.
        ( D ) VOLUME: 261
        ( F ) PAGES: 3676-3680
        ( G ) DATE: 1986
        ( A ) AUTHORS: Wakabayashi, T.
                Kato, H.
                Tachibaba, S.
        ( C ) JOURNAL: Nucleic Acids Research
        ( D ) VOLUME: 13
        ( F ) PAGES: 1817-1828
        ( G ) DATE: 1985
        ( A ) AUTHORS: Gibson, B.W.
                Poulter, L.
                Williams, D.H.
                Maggio, J.E.
        ( C ) JOURNAL: J. Biol. Chem.
        ( D ) VOLUME: 261
        ( F ) PAGES: 5341-5349
        ( G ) DATE: 1986
        ( H ) DOCUMENT NUMBER: WO90/04407
        ( I ) FILING DATE: 16-OCT-1989
        ( J ) PUBLICATION DATE: 03-MAY-1990

( x i ) SEQUENCE DESCRIPTION: SEQ ID NO:19:

```
Gly  Phe  Gly  Ser  Phe  Leu  Gly  Lys  Ala  Leu
                5                          10

Lys  Ala  Ala  Leu  Lys  Ile  Gly  Ala  Asn  Ala
                15                         20

Leu  Gly  Gly  Ala  Pro  Gln  Gln
                25
```

( 2 ) INFORMATION FOR SEQ ID NO:20:

( i ) SEQUENCE CHARACTERISTICS:
        ( A ) LENGTH: 27 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: CPF peptide.

( x ) PUBLICATION INFORMATION:
        ( A ) AUTHORS: Richter, K.
                Egger, R.
                Kreil
        ( C ) JOURNAL: J. Biol. Chem.

(D) VOLUME: 261
(F) PAGES: 3676-3680
(G) DATE: 1986
(A) AUTHORS: Wakabayashi, T.
    Kato, H.
    Tachibaba, S.
(C) JOURNAL: Nucleic Acids Research
(D) VOLUME: 13
(F) PAGES: 1817-1828
(G) DATE: 1985
(A) AUTHORS: Gibson, B.W.
    Poulter, L.
    Williams, D.H.
    Maggio, J.E.
(C) JOURNAL: J. Biol. Chem.
(D) VOLUME: 261
(F) PAGES: 5341-5349
(G) DATE: 1986
(H) DOCUMENT NUMBER: WO90/04407
(I) FILING DATE: 16-OCT-1989
(J) PUBLICATION DATE: 03-MAY-1990

(xi) SEQUENCE DESCRIPTION: SEQ ID NO:20:

```
Gly Phe Gly Ser Phe Leu Gly Lys Ala Leu
                 5                      10

Lys Ala Ala Leu Lys Ile Gly Ala Asn Ala
                15                      20

Leu Gly Gly Ser Pro Gln Gln
                25
```

(2) INFORMATION FOR SEQ ID NO:21:

(i) SEQUENCE CHARACTERISTICS:
    (A) LENGTH: 27 amino acids
    (B) TYPE: amino acid
    (C) STRANDEDNESS:
    (D) TOPOLOGY: linear (ii) MOLECULE TYPE: peptide (ix) FEATURE:
    (A) NAME/KEY: CPF peptide.

(x) PUBLICATION INFORMATION:
    (A) AUTHORS: Richter, K.
        Egger, R.
        Kreil
    (C) JOURNAL: J. Biol. Chem.
    (D) VOLUME: 261
    (F) PAGES: 3676-3680
    (G) DATE: 1986
    (A) AUTHORS: Wakabayashi, T.
        Kato, H.
        Tachibaba, S.
    (C) JOURNAL: Nucleic Acids Research
    (D) VOLUME: 13
    (F) PAGES: 1817-1828
    (G) DATE: 1985
    (A) AUTHORS: Gibson, B.W.
        Poulter, L.
        Williams, D.H.
        Maggio, J.E.
    (C) JOURNAL: J. Biol. Chem.
    (D) VOLUME: 261
    (F) PAGES: 5341-5349
    (G) DATE: 1986
    (H) DOCUMENT NUMBER: WO90/04407
    (I) FILING DATE: 16-OCT-1989
    (J) PUBLICATION DATE: 03-MAY-1990

(xi) SEQUENCE DESCRIPTION: SEQ ID NO:21:

```
Gly  Phe  Ala  Ser  Phe  Leu  Gly  Lys  Ala  Leu
                    5                        10

Lys  Ala  Ala  Leu  Lys  Ile  Gly  Ala  Asn  Leu
                    15                       20

Leu  Gly  Gly  Thr  Pro  Gln  Gln
                    25
```

( 2 ) INFORMATION FOR SEQ ID NO:22:

( i ) SEQUENCE CHARACTERISTICS:
        ( A ) LENGTH: 27 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: CPF peptide.

( x ) PUBLICATION INFORMATION:
        ( A ) AUTHORS: Richter, K.
            Egger, R.
            Kreil
        ( C ) JOURNAL: J. Biol. Chem.
        ( D ) VOLUME: 261
        ( F ) PAGES: 3676-3680
        ( G ) DATE: 1986
        ( A ) AUTHORS: Wakabayashi, T.
            Kato, H.
            Tachibaba, S.
        ( C ) JOURNAL: Nucleic Acids Research
        ( D ) VOLUME: 13
        ( F ) PAGES: 1817-1828
        ( G ) DATE: 1985
        ( A ) AUTHORS: Gibson, B.W.
            Poulter, L.
            Williams, D.H.
            Maggio, J.E.
        ( C ) JOURNAL: J. Biol. Chem.
        ( D ) VOLUME: 261
        ( F ) PAGES: 5341-5349
        ( G ) DATE: 1986

( x i ) SEQUENCE DESCRIPTION: SEQ ID NO:22:

```
Gly  Phe  Ala  Ser  Phe  Leu  Gly  Lys  Ala  Leu
                    5                        10

Lys  Ala  Ala  Leu  Lys  Ile  Gly  Ala  Asn  Ala
                    15                       20

Leu  Gly  Gly  Ala  Pro  Gln  Gln
                    25
```

( 2 ) INFORMATION FOR SEQ ID NO:23:

( i ) SEQUENCE CHARACTERISTICS:
        ( A ) LENGTH: 27 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: CPF peptide.

( x ) PUBLICATION INFORMATION:
        ( A ) AUTHORS: Richter, K.
            Egger, R.
            Kreil
        ( C ) JOURNAL: J. Biol. Chem.
        ( D ) VOLUME: 261
        ( F ) PAGES: 3676-3680
        ( G ) DATE: 1986

(A) AUTHORS: Wakabayashi, T.
    Kato, H.
    Tachibaba, S.
(C) JOURNAL: Nucleic Acids Research
(D) VOLUME: 13
(F) PAGES: 1817-1828
(G) DATE: 1985
(A) AUTHORS: Gibson, B.W.
    Poulter, L.
    Williams, D.H.
    Maggio, J.E.
(C) JOURNAL: J. Biol. Chem.
(D) VOLUME: 261
(F) PAGES: 5341-5349
(G) DATE: 1986

(x i) SEQUENCE DESCRIPTION: SEQ ID NO:23:

Gly Phe Ala Ser Phe Leu Gly Lys Ala Leu
                  5                   10

Lys Ala Ala Leu Lys Ile Gly Ala Asn Met
                 15                   20

Leu Gly Gly Ala Pro Gln Gln
                 25

(2) INFORMATION FOR SEQ ID NO:24:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: CPF peptide.

(x) PUBLICATION INFORMATION:
        (A) AUTHORS: Richter, K.
            Egger, R.
            Kreil
        (C) JOURNAL: J. Biol. Chem.
        (D) VOLUME: 261
        (F) PAGES: 3676-3680
        (G) DATE: 1986
        (A) AUTHORS: Wakabayashi, T.
            Kato, H.
            Tachibaba, S.
        (C) JOURNAL: Nucleic Acids Research
        (D) VOLUME: 13
        (F) PAGES: 1817-1828
        (G) DATE: 1985
        (A) AUTHORS: Gibson, B.W.
            Poulter, L.
            Williams, D.H.
            Maggio, J.E.
        (C) JOURNAL: J. Biol. Chem.
        (D) VOLUME: 261
        (F) PAGES: 5341-5349
        (G) DATE: 1986

(x i) SEQUENCE DESCRIPTION: SEQ ID NO:24:

Gly Phe Gly Ser Phe Leu Gly Lys Ala Leu
                  5                   10

Lys Ala Ala Leu Lys Ile Gly Ala Asn Ala
                 15                   20

Leu Gly Gly Ser Leu Gln Gln
                 25

(2) INFORMATION FOR SEQ ID NO:25:

(i) SEQUENCE CHARACTERISTICS:

(A) LENGTH: 27 amino acids
(B) TYPE: amino acid
(C) STRANDEDNESS:
(D) TOPOLOGY: linear (ii) MOLECULE TYPE: peptide (ix) FEATURE:
(A) NAME/KEY: CPF peptide.

(x) PUBLICATION INFORMATION:
(A) AUTHORS: Richter, K.
Egger, R.
Kreil
(C) JOURNAL: J. Biol. Chem.
(D) VOLUME: 261
(F) PAGES: 3676-3680
(G) DATE: 1986
(A) AUTHORS: Wakabayashi, T.
Kato, H.
Tachibaba, S.
(C) JOURNAL: Nucleic Acids Research
(D) VOLUME: 13
(F) PAGES: 1817-1828
(G) DATE: 1985
(A) AUTHORS: Gibson, B.W.
Poulter, L.
Williams, D.H.
Maggio, J.E.
(C) JOURNAL: J. Biol. Chem.
(D) VOLUME: 261
(F) PAGES: 5341-5349
(G) DATE: 1986

(xi) SEQUENCE DESCRIPTION: SEQ ID NO:25:

Gly Phe Gly Ser Phe Leu Gly Lys Ala Leu
                  5                  10

Lys Ala Gly Leu Lys Ile Gly Thr Asn Phe
               15                  20

Leu Gly Gly Ala Pro Gln Gln
               25

(2) INFORMATION FOR SEQ ID NO:26:

(i) SEQUENCE CHARACTERISTICS:
(A) LENGTH: 27 amino acids
(B) TYPE: amino acid
(C) STRANDEDNESS:
(D) TOPOLOGY: linear (ii) MOLECULE TYPE: peptide (ix) FEATURE:
(A) NAME/KEY: CPF peptide.

(x) PUBLICATION INFORMATION:
(A) AUTHORS: Richter, K
Egger, R.
Kreil
(C) JOURNAL: J. Biol. Chem.
(D) VOLUME: 261
(F) PAGES: 3676-3680
(G) DATE: 1986
(A) AUTHORS: Wakabayashi, T.
Kato, H.
Tachibaba, S.
(C) JOURNAL: Nucleic Acids Research
(D) VOLUME: 13
(F) PAGES: 1817-1828
(G) DATE: 1985
(A) AUTHORS: Gibson, B.W.
Poulter, L.
Williams, D.H.
Maggio, J.E.
(C) JOURNAL: J. Biol. Chem.
(D) VOLUME: 261

(F) PAGES: 5341-5349
(G) DATE: 1986

(xi) SEQUENCE DESCRIPTION: SEQ ID NO:26:

Gly Leu Ala Ser Leu Leu Gly Lys Ala Leu
                  5                    10

Lys Ala Ala Leu Lys Ile Gly Ala Asn Ala
               15                    20

Leu Gly Gly Ser Pro Gln Gln
                 25

(2) INFORMATION FOR SEQ ID NO:27:

(i) SEQUENCE CHARACTERISTICS:
    (A) LENGTH: 21 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:27:

Lys Ile Ala Gly Lys Ile Ala Lys Ile Ala
                  5                    10

Gly Lys Ile Ala Lys Ile Ala Gly Lys Ile
                 15                    20

Ala (2) INFORMATION FOR SEQ ID NO:28:

(i) SEQUENCE CHARACTERISTICS:
    (A) LENGTH: 21 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:28:

Lys Ile Ala Lys Ile Ala Gly Lys Ile Ala
                  5                    10

Lys Ile Ala Gly Lys Ile Ala Lys Ile Ala
                 15                    20

Gly (2) INFORMATION FOR SEQ ID NO:29:

(i) SEQUENCE CHARACTERISTICS:
    (A) LENGTH: 21 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:29:

Lys Ile Ala Gly Lys Ile Gly Lys Ile Ala
                  5                    10

Gly Lys Ile Gly Lys Ile Ala Gly Lys Ile
                 15                    20

Gly (2) INFORMATION FOR SEQ ID NO:30:

( i ) SEQUENCE CHARACTERISTICS:
  ( A ) LENGTH: 21 amino acids
  ( B ) TYPE: amino acid
  ( C ) STRANDEDNESS:
  ( D ) TOPOLOGY: linear ( i i ) MOLECULE TYPE: peptide ( x i ) SEQUENCE DESCRIPTION: SEQ ID NO:30:

Lys Leu Ala Gly Lys Leu Ala Lys Leu Ala
                  5                   10
Gly Lys Leu Ala Lys Leu Ala Gly Lys Leu
                 15                   20
Ala ( 2 ) INFORMATION FOR SEQ ID NO:31:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:31:

Lys Phe Ala Gly Lys Phe Ala Lys Phe Ala
                  5                   10
Gly Lys Phe Ala Lys Phe Ala Gly Lys Phe
                 15                   20
Ala ( 2 ) INFORMATION FOR SEQ ID NO:32:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:32:

Lys Ala Leu Ser Lys Ala Leu Lys Ala Leu
                  5                   10
Ser Lys Ala Leu Lys Ala Leu Ser Lys Ala
                 15                   20
Leu ( 2 ) INFORMATION FOR SEQ ID NO:33:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:33:

Lys Leu Leu Lys Ala Leu Gly Lys Leu Leu
                  5                   10
Lys Ala Leu Gly Lys Leu Leu Lys Ala Leu
                 15                   20
Gly ( 2 ) INFORMATION FOR SEQ ID NO:34:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:34:

```
Lys  Ala  Ile  Gly  Lys  Ala  Ile  Lys  Ala  Ile
                    5                             10
Gly  Lys  Ala  Ile  Lys  Ala  Ile  Gly  Lys  Ala
                   15                             20
Ile
```

( 2 ) INFORMATION FOR SEQ ID NO:35:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:35:

```
Gly  Ile  Ala  Lys  Ile  Ala  Lys  Gly  Ile  Ala
                    5                             10
Lys  Ile  Ala  Lys  Gly  Ile  Ala  Lys  Ile  Ala
                   15                             20
Lys
```

( 2 ) INFORMATION FOR SEQ ID NO:36:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:36:

```
Lys  Ile  Ala  Lys  Ile  Phe  Gly  Lys  Ile  Ala
                    5                             10
Lys  Ile  Phe  Gly  Lys  Ile  Ala  Lys  Ile  Phe
                   15                             20
Gly
```

( 2 ) INFORMATION FOR SEQ ID NO:37:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:37:

```
Gly Ile Ala Arg Ile Ala Lys Gly Ile Ala
                 5                      10
Arg Ile Ala Lys Gly Ile Ala Arg Ile Ala
                 15                     20
Lys
```

( 2 ) INFORMATION FOR SEQ ID NO:38:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:38:

```
Lys Phe Ala Arg Ile Ala Gly Lys Phe Ala
                 5                      10
Arg Ile Ala Gly Lys Phe Ala Arg Ile Ala
                 15                     20
Gly
```

( 2 ) INFORMATION FOR SEQ ID NO:39:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:39:

```
Gly Phe Ala Lys Ile Ala Lys Gly Phe Ala
                 5                      10
Lys Ile Ala Lys Gly Phe Ala Lys Ile Ala
                 15                     20
Lys
```

( 2 ) INFORMATION FOR SEQ ID NO:40:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: Xaa is ornithine ( x i ) SEQUENCE DESCRIPTION: SEQ ID NO:40:

```
Lys Ile Ala Gly Xaa Ile Ala Lys Ile Ala
                 5                      10
Gly Xaa Ile Ala Lys Ile Ala Gly Xaa Ile
                 15                     20
Ala
```

( 2 ) INFORMATION FOR SEQ ID NO:41:

( i ) SEQUENCE CHARACTERISTICS:
        ( A ) LENGTH: 21 amino acids
        ( B ) TYPE: amino acid ( C ) STRANDEDNESS:
( D ) TOPOLOGY: linear ( i i ) MOLECULE TYPE: peptide ( x i ) SEQUENCE DESCRIPTION: SEQ ID NO:41:

Lys Ile Ala Arg Ile Ala Gly Lys Ile Ala
                  5                   10

Arg Ile Ala Gly Lys Ile Ala Arg Ile Ala
                15                  20

Gly ( 2 ) INFORMATION FOR SEQ ID NO:42:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( D ) OTHER INFORMATION: Xaa is ornithine ( x i ) SEQUENCE DESCRIPTION: SEQ ID NO:42:

Xaa Ile Ala Gly Lys Ile Ala Xaa Ile Ala
                  5                   10

Gly Lys Ile Ala Xaa Ile Ala Gly Lys Ile
                15                  20

Ala ( 2 ) INFORMATION FOR SEQ ID NO:43:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:43:

Gly Ile Ala Arg Ile Phe Lys Gly Ile Ala
                  5                   10

Arg Ile Phe Lys Gly Ile Ala Arg Ile Phe
                15                  20

Lys ( 2 ) INFORMATION FOR SEQ ID NO:44:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( D ) OTHER INFORMATION: Xaa is norleucine.

( x i ) SEQUENCE DESCRIPTION: SEQ ID NO:44:

```
Lys  Xaa  Ala  Gly  Lys  Xaa  Ala  Lys  Xaa  Ala
                   5                        10

Gly  Lys  Xaa  Ala  Lys  Xaa  Ala  Gly  Lys  Xaa
                  15                        20

Ala
```

( 2 ) INFORMATION FOR SEQ ID NO:45:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: Xaa is norleucine.

( x i ) SEQUENCE DESCRIPTION: SEQ ID NO:45:

```
Lys  Xaa  Ala  Gly  Lys  Ile  Ala  Lys  Xaa  Ala
                   5                        10

Gly  Lys  Ile  Ala  Lys  Xaa  Ala  Gly  Lys  Ile
                  15                        20

Ala
```

( 2 ) INFORMATION FOR SEQ ID NO:46:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: Xaa is norleucine.

( x i ) SEQUENCE DESCRIPTION: SEQ ID NO:46:

```
Lys  Ile  Ala  Gly  Lys  Xaa  Ala  Lys  Ile  Ala
                   5                        10

Gly  Lys  Xaa  Ala  Lys  Ile  Ala  Gly  Lys  Xaa
                  15                        20

Ala
```

( 2 ) INFORMATION FOR SEQ ID NO:47:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: Xaa is norvaline.

( x i ) SEQUENCE DESCRIPTION: SEQ ID NO:47:

```
Lys  Xaa  Ala  Gly  Lys  Xaa  Ala  Lys  Xaa  Ala
                   5                        10

Gly  Lys  Xaa  Ala  Lys  Xaa  Ala  Gly  Lys  Xaa
                  15                        20

Ala
```

( 2 ) INFORMATION FOR SEQ ID NO:48:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: Xaa is norvaline.

( x i ) SEQUENCE DESCRIPTION: SEQ ID NO:48:

Lys Xaa Ala Gly Lys Ile Ala Lys Xaa Ala
                5                          10

Gly Lys Ile Ala Lys Xaa Ala Gly Lys Xaa
               15                        20

Ala ( 2 ) INFORMATION FOR SEQ ID NO:49:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:49:

Lys Leu Leu Ser Lys Leu Gly Lys Leu Leu
                5                          10

Ser Lys Leu Gly Lys Leu Leu Ser Lys Leu
               15                       20

Gly ( 2 ) INFORMATION FOR SEQ ID NO:50:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:50:

Lys Leu Leu Ser Lys Phe Gly Lys Leu Leu
                5                          10

Ser Lys Phe Gly Lys Leu Leu Ser Lys Phe
               15                       20

Gly ( 2 ) INFORMATION FOR SEQ ID NO:51:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: Xaa is norvaline.

( x i ) SEQUENCE DESCRIPTION: SEQ ID NO:51:

Lys Ile Ala Gly Lys Xaa Ala Lys Ile Ala
                    5                   10
Gly Lys Xaa Ala Lys Ile Ala Gly Lys Xaa
                15                  20
Ala ( 2 ) INFORMATION FOR SEQ ID NO:52:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:52:

His Ile Ala Gly His Ile Ala His Ile Ala
                    5                   10
Gly His Ile Ala His Ile Ala Gly His Ile
                15                  20
Ala ( 2 ) INFORMATION FOR SEQ ID NO:53:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:53:

Ala Gly Lys Ile Ala Lys Ile Ala Gly Lys
                    5                   10
Ile Ala Lys Ile Ala Gly Lys Ile Ala Lys
                15                  20
Ile ( 2 ) INFORMATION FOR SEQ ID NO:54:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:54:

Ile Ala Lys Ile Ala Gly Lys Ile Ala Lys
                    5                   10
Ile Ala Gly Lys Ile Ala Lys Ile Ala Gly
                15                  20
Lys ( 2 ) INFORMATION FOR SEQ ID NO:55:

( i ) SEQUENCE CHARACTERISTICS:
        ( A ) LENGTH: 21 amino acids
        ( B ) TYPE: amino acid
        ( C ) STRANDEDNESS:

(D) TOPOLOGY: linear (ii) MOLECULE TYPE: peptide (xi) SEQUENCE DESCRIPTION: SEQ ID NO:55:

Lys Ile Ala Gly Arg Ile Ala Lys Ile Ala
                 5                   10
Gly Arg Ile Ala Lys Ile Ala Gly Arg Ile
                 15                  20
Ala (2) INFORMATION FOR SEQ ID NO:56:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:56:

Arg Ile Ala Gly Arg Ile Ala Arg Ile Ala
                 5                   10
Gly Arg Ile Ala Arg Ile Ala Gly Arg Ile
                 15                  20
Ala (2) INFORMATION FOR SEQ ID NO:57:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:57:

Lys Val Ala Gly Lys Ile Ala Lys Val Ala
                 5                   10
Gly Lys Ile Ala Lys Val Ala Gly Lys Ile
                 15                  20
Ala (2) INFORMATION FOR SEQ ID NO:58:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:58:

Lys Ile Ala Gly Lys Val Ala Lys Ile Ala
                 5                   10
Gly Lys Val Ala Lys Ile Ala Gly Lys Val
                 15                  20
Ala (2) INFORMATION FOR SEQ ID NO:59:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:59:

```
Ala Lys Ile Ala Gly Lys Ile Ala Lys Ile
              5                        10
Ala Gly Lys Ile Ala Lys Ile Ala Gly Lys
             15                        20
Ile
```

( 2 ) INFORMATION FOR SEQ ID NO:60:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( D ) OTHER INFORMATION: Xaa is ornithine.

( x i ) SEQUENCE DESCRIPTION: SEQ ID NO:60:

```
Xaa Ile Ala Gly Xaa Ile Ala Xaa Ile Ala
              5                        10
Gly Xaa Ile Ala Xaa Ile Ala Gly Xaa Ile
             15                        20
Ala
```

( 2 ) INFORMATION FOR SEQ ID NO:61:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:61:

```
Lys Phe Ala Gly Lys Ile Ala Lys Phe Ala
              5                        10
Gly Lys Ile Ala Lys Phe Ala Gly Lys Ile
             15                        20
Ala
```

( 2 ) INFORMATION FOR SEQ ID NO:62:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:62:

Lys Ile Ala Gly Lys Phe Ala Lys Ile Ala
                5                       10

Gly Lys Phe Ala Lys Ile Ala Gly Lys Phe
                15                      20

Ala ( 2 ) INFORMATION FOR SEQ ID NO:63:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: Xaa is cyclohexylalanine.

( x i ) SEQUENCE DESCRIPTION: SEQ ID NO:63:

Lys Xaa Ala Gly Lys Ile Ala Lys Xaa Ala
                5                       10

Gly Lys Ile Ala Lys Xaa Ala Gly Lys Ile
                15                      20

Ala ( 2 ) INFORMATION FOR SEQ ID NO:64:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: Xaa is norleucine.

( x i ) SEQUENCE DESCRIPTION: SEQ ID NO:64:

Lys Xaa Ala Lys Ile Ala Gly Lys Xaa Ala
                5                       10

Lys Ile Ala Gly Lys Xaa Ala Lys Ile Ala
                15                      20

Gly ( 2 ) INFORMATION FOR SEQ ID NO:65:

( i ) SEQUENCE CHARACTERISTICS:
        ( A ) LENGTH: 21 AMINO ACIDS
        ( B ) TYPE: amino acids
        ( C ) STRANDEDNESS:
        ( D ) TOPOLOGY: linear ( i i ) MOLECULE TYPE: peptide ( x i ) SEQUENCE DESCRIPTION: SEQ ID NO:65:

Arg Ile Ala Gly Lys Ile Ala Arg Ile Ala
                5                       10

Gly Lys Ile Ala Arg Ile Ala Gly Lys Ile
                15                      20

Ala ( 2 ) INFORMATION FOR SEQ ID NO:66:

( i ) SEQUENCE CHARACTERISTICS:
  ( A ) LENGTH: 21 amino acids
  ( B ) TYPE: amino acid
  ( C ) STRANDEDNESS:
  ( D ) TOPOLOGY: linear ( i i ) MOLECULE TYPE: peptide ( i x ) FEATURE:
  ( D ) OTHER INFORMATION: Xaa is homoarginine.

( x i ) SEQUENCE DESCRIPTION: SEQ ID NO:66:

Xaa Ile Ala Gly Xaa Ile Ala Xaa Ile Ala
                  5                              10
Gly Xaa Ile Ala Xaa Ile Ala Gly Xaa Ile
                 15                              20
Ala ( 2 ) INFORMATION FOR SEQ ID NO:67:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE: Xaa is p-aminophenylalanine ( x i ) SEQUENCE DESCRIPTION: SEQ ID NO:67:

Xaa Ile Ala Gly Lys Ile Ala Xaa Ile Ala
                  5                              10
Gly Lys Ile Ala Xaa Ile Ala Gly Lys Ile
                 15                              20
Ala ( 2 ) INFORMATION FOR SEQ ID NO:68:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE: Xaa is p-aminophenylalanine ( x i ) SEQUENCE DESCRIPTION: SEQ ID NO:68:

Lys Ile Ala Gly Xaa Ile Ala Lys Ile Ala
                  5                              10
Gly Xaa Ile Ala Lys Ile Ala Gly Xaa Ile
                 15                              20
Ala ( 2 ) INFORMATION FOR SEQ ID NO:69:

( i ) SEQUENCE CHARACTERISTICS:
    ( A ) LENGTH: 24 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:69:

-continued

```
Lys  Ile  Ala  Lys  Ile  Ala  Gly  Lys  Ile  Ala
                    5                        10

Lys  Ile  Ala  Gly  Lys  Ile  Ala  Lys  Ile  Ala
                    15                       20

Gly  Lys  Ile  Ala
```

( 2 ) INFORMATION FOR SEQ ID NO:70:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:70:

```
Lys  Leu  Ala  Ser  Lys  Ala  Gly  Lys  Ile  Ala  Gly
                    5                        10

Lys  Ile  Ala  Lys  Val  Ala  Leu  Lys  Ala  Leu
                    15                       20
```

( 2 ) INFORMATION FOR SEQ ID NO:71:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: Xaa is ornithine.

( x i ) SEQUENCE DESCRIPTION: SEQ ID NO:71:

```
Lys  Ile  Ala  Gly  Lys  Ile  Ala  Lys  Ile  Ala  Gly
                    5                        10

Xaa  Ile  Ala  Lys  Ile  Ala  Gly  Lys  Ile  Ala
                    15                       20
```

( 2 ) INFORMATION FOR SEQ ID NO:72:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:72:

```
Lys  Ile  Ala  Gly  Lys  Ile  Ala  Lys  Ile  Ala
                    5                        10

Gly  Arg  Ile  Ala  Lys  Ile  Ala  Gly  Lys  Ile
                    15                       20

Ala
```

( 2 ) INFORMATION FOR SEQ ID NO:73:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
    ( D ) OTHER INFORMATION: Xaa is norleucine.

( x i ) SEQUENCE DESCRIPTION: SEQ ID NO:73:

Lys Ile Ala Gly Lys Ile Ala Lys Ile Ala
                  5                    10
Gly Xaa Ile Ala Lys Ile Ala Gly Lys Ile
                 15                    20
Ala ( 2 ) INFORMATION FOR SEQ ID NO:74:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: Xaa is norvaline.

( x i ) SEQUENCE DESCRIPTION: SEQ ID NO:74:

Lys Ile Ala Gly Lys Ile Ala Lys Ile Ala
                  5                    10
Gly Xaa Ile Ala Lys Ile Ala Gly Lys Ile
                 15                    20
Ala ( 2 ) INFORMATION FOR SEQ ID NO:75:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: Xaa is ornithine.

( x i ) SEQUENCE DESCRIPTION: SEQ ID NO:75:

Lys Phe Ala Gly Lys Phe Ala Lys Phe Ala Gly
                  5                    10
Xaa Phe Ala Lys Phe Ala Gly Lys Phe Ala
                 15                    20

( 2 ) INFORMATION FOR SEQ ID NO:76:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: Xaa is ornithine.

( x i ) SEQUENCE DESCRIPTION: SEQ ID NO:76:

```
Lys  Ile  Ala  Gly  Lys  Phe  Ala  Lys  Ile  Ala
                   5                          10

Gly  Xaa  Phe  Ala  Lys  Ile  Ala  Gly  Lys  Phe
                   15                         20

Ala
```

( 2 ) INFORMATION FOR SEQ ID NO:77:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: Xaa at residues 6, 13, and 20 is norleucine; Xaa at residue 12 is ornithine.

( x i ) SEQUENCE DESCRIPTION: SEQ ID NO:77:

```
Lys  Ile  Ala  Gly  Lys  Xaa  Ala  Lys  Ile  Ala
                   5                          10

Gly  Xaa  Xaa  Ala  Lys  Ile  Ala  Gly  Lys  Xaa
                   15                         20

Ala
```

( 2 ) INFORMATION FOR SEQ ID NO:78:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:78:

```
Lys  Met  Ala  Ser  Lys  Ala  Gly  Lys  Ile  Ala
                   5                          10

Gly  Lys  Ile  Ala  Lys  Val  Ala  Leu  Lys  Ala
                   15                         20

Leu
```

( 2 ) INFORMATION FOR SEQ ID NO:79:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:79:

```
Lys  Ile  Ala  Ser  Lys  Ala  Gly  Lys  Ile  Ala
                   5                          10

Gly  Lys  Ile  Ala  Lys  Val  Ala  Leu  Lys  Ala  Leu
                   15                         20
```

( 2 ) INFORMATION FOR SEQ ID NO:80:

( i ) SEQUENCE CHARACTERISTICS:
        ( A ) LENGTH: 21 amino acids
        ( B ) TYPE: amino acid (C) STRANDEDNESS:
(D) TOPOLOGY: linear (ii) MOLECULE TYPE: peptide (ix) FEATURE:
    (D) OTHER INFORMATION: Xaa is norleucine.

(xi) SEQUENCE DESCRIPTION: SEQ ID NO:80:

Lys Ile Ala Ser Lys Ala Gly Lys Xaa Ala
              5                   10

Gly Lys Ile Ala Lys Val Ala Leu Lys Ala Leu
             15                  20

(2) INFORMATION FOR SEQ ID NO:81:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (ix) FEATURE:
        (D) OTHER INFORMATION: Xaa is norleucine.

(xi) SEQUENCE DESCRIPTION: SEQ ID NO:81:

Lys Leu Ala Ser Lys Ala Gly Lys Xaa Ala
              5                   10

Gly Lys Ile Ala Lys Val Ala Leu Lys Ala
             15                  20

Leu (2) INFORMATION FOR SEQ ID NO:82:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (ix) FEATURE:
        (D) OTHER INFORMATION: Xaa is norleucine.

(xi) SEQUENCE DESCRIPTION: SEQ ID NO:82:

Lys Xaa Ala Ser Lys Ala Gly Lys Xaa Ala
              5                   10

Gly Lys Ile Ala Lys Val Ala Leu Lys Ala Leu
             15                  20

(2) INFORMATION FOR SEQ ID NO:83:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (ix) FEATURE:
        (D) OTHER INFORMATION: Xaa is p-aminophenylalanine.

(xi) SEQUENCE DESCRIPTION: SEQ ID NO:83:

Lys Ile Ala Gly Lys Ile Ala Lys Ile Ala
                  5                   10

Gly Xaa Ile Ala Lys Ile Ala Gly Lys Ile
                 15                   20

Ala ( 2 ) INFORMATION FOR SEQ ID NO:84:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:84:

Lys Ile Ala Gly Ala Ile Ala Lys Ile Ala
                  5                   10

Gly Lys Ile Ala Lys Ile Ala Gly Lys Ile
                 15                   20

Ala ( 2 ) INFORMATION FOR SEQ ID NO:85:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:85:

Lys Ile Ala Gly Lys Ile Ala Lys Ile Ala
                  5                   10

Gly Ala Ile Ala Lys Ile Ala Gly Lys Ile
                 15                   20

Ala ( 2 ) INFORMATION FOR SEQ ID NO:86:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:86:

Lys Ile Ala Gly Lys Ile Ala Lys Ile Ala
                  5                   10

Gly Lys Ile Ala Lys Ile Ala Gly Ala Ile
                 15                   20

Ala ( 2 ) INFORMATION FOR SEQ ID NO:87:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear (i i) MOLECULE TYPE: peptide (x i) SEQUENCE DESCRIPTION: SEQ ID NO:87:

Lys Leu Ala Ser Lys Ala Ala Lys Ile Ala
              5                      10
Ala Lys Ile Ala Lys Val Ala Leu Lys Ala
              10                     20
Leu (2) INFORMATION FOR SEQ ID NO:88:

(i) SEQUENCE CHARACTERISTICS:
        (A) LENGTH: 21 amino acids
        (B) TYPE: amino acid
        (C) STRANDEDNESS:
        (D) TOPOLOGY: linear (i i) MOLECULE TYPE: peptide (x i) SEQUENCE DESCRIPTION: SEQ ID NO:88:

Lys Ile Ala Lys Lys Ile Ala Lys Ile Ala
              5                      10
Lys Lys Ile Ala Lys Ile Ala Lys Lys Ile
              15                     20
Ala (2) INFORMATION FOR SEQ ID NO:89:

(i) SEQUENCE CHARACTERISTICS:
        (A) LENGTH: 21 amino acids
        (B) TYPE: amino acid
        (C) STRANDEDNESS:
        (D) TOPOLOGY: linear (i i) MOLECULE TYPE: peptide (x i) SEQUENCE DESCRIPTION: SEQ ID NO:89:

Lys Phe Ala Lys Lys Phe Ala Lys Phe Ala
              5                      10
Lys Lys Phe Ala Lys Phe Ala Lys Lys Phe
              15                     20
Ala (2) INFORMATION FOR SEQ ID NO:90:

(i) SEQUENCE CHARACTERISTICS:
        (A) LENGTH: 21 amino acids
        (B) TYPE: amino acid
        (C) STRANDEDNESS:
        (D) TOPOLOGY: linear (i i) MOLECULE TYPE: peptide (x i) SEQUENCE DESCRIPTION: SEQ ID NO:90:

Lys Phe Ala Lys Lys Ile Ala Lys Phe Ala
              5                      10
Lys Lys Ile Ala Lys Phe Ala Lys Lys Ile
              15                     20
Ala (2) INFORMATION FOR SEQ ID NO:91:

(i) SEQUENCE CHARACTERISTICS:
        (A) LENGTH: 21 amino acids (B) TYPE: amino acid
(C) STRANDEDNESS:
(D) TOPOLOGY: linear (ii) MOLECULE TYPE: peptide (xi) SEQUENCE DESCRIPTION: SEQ ID NO:91:

| Ala | Ile | Ala | Gly | Lys | Ile | Ala | Lys | Ile | Ala |
|-----|-----|-----|-----|-----|-----|-----|-----|-----|-----|
|     |     |     |     | 5   |     |     |     |     | 10  |

| Gly | Lys | Ile | Ala | Lys | Ile | Ala | Gly | Lys | Ile |
|-----|-----|-----|-----|-----|-----|-----|-----|-----|-----|
|     |     |     |     | 15  |     |     |     |     | 20  |

Ala (2) INFORMATION FOR SEQ ID NO:92:

(i) SEQUENCE CHARACTERISTICS:
(A) LENGTH: 21 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:92:

| Lys | Ile | Ala | Gly | Lys | Ile | Ala | Ala | Ile | Ala |
|-----|-----|-----|-----|-----|-----|-----|-----|-----|-----|
|     |     |     |     | 5   |     |     |     |     | 10  |

| Gly | Lys | Ile | Ala | Lys | Ile | Ala | Gly | Lys | Ile |
|-----|-----|-----|-----|-----|-----|-----|-----|-----|-----|
|     |     |     |     | 15  |     |     |     |     | 20  |

Ala (2) INFORMATION FOR SEQ ID NO:93:

(i) SEQUENCE CHARACTERISTICS:
(A) LENGTH: 21 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:93:

| Lys | Ile | Ala | Gly | Lys | Ile | Ala | Lys | Ile | Ala |
|-----|-----|-----|-----|-----|-----|-----|-----|-----|-----|
|     |     |     |     | 5   |     |     |     |     | 10  |

| Gly | Lys | Ile | Ala | Ala | Ile | Ala | Gly | Lys | Ile |
|-----|-----|-----|-----|-----|-----|-----|-----|-----|-----|
|     |     |     |     | 15  |     |     |     |     | 20  |

Ala (2) INFORMATION FOR SEQ ID NO:94:

(i) SEQUENCE CHARACTERISTICS:
(A) LENGTH: 21 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:94:

| Gly | Met | Ala | Ser | Lys | Ala | Gly | Lys | Ile | Ala |
|-----|-----|-----|-----|-----|-----|-----|-----|-----|-----|
|     |     |     |     | 5   |     |     |     |     | 10  |

| Gly | Lys | Ile | Ala | Lys | Val | Ala | Leu | Lys | Ala |
|-----|-----|-----|-----|-----|-----|-----|-----|-----|-----|
|     |     |     |     | 15  |     |     |     |     | 20  |

Leu ( 2 ) INFORMATION FOR SEQ ID NO:95:

( i ) SEQUENCE CHARACTERISTICS:
        ( A ) LENGTH: 11 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION:SEQ ID NO:95:

Leu Lys Lys Leu Lys Lys Leu Leu Lys Leu
                    5                     10

Leu ( 2 ) INFORMATION FOR SEQ ID NO:96:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION:SEQ ID NO:96:

Leu Leu Lys Lys Leu Lys Lys Leu Leu Lys
                    5                     10

Leu Leu ( 2 ) INFORMATION FOR SEQ ID NO:97:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION:SEQ ID NO:97:

Lys Leu Leu Lys Lys Leu Lys Lys Leu Leu
                    5                     10

Lys Leu Leu ( 2 ) INFORMATION FOR SEQ ID NO:98:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION:SEQ ID NO:98:

Lys Lys Leu Leu Lys Lys Leu Lys Lys Leu
                    5                     10

Leu Lys Leu Leu ( 2 ) INFORMATION FOR SEQ ID NO:99:

( i ) SEQUENCE CHARACTERISTICS:
        ( A ) LENGTH: 16 amino acids
        ( B ) TYPE: amino acid
        ( C ) STRANDEDNESS:
        ( D ) TOPOLOGY: linear (i i) MOLECULE TYPE: peptide (i x) SEQUENCE DESCRIPTION: SEQ ID NO:99:

Lys Lys Leu Leu Lys Lys Leu Lys Lys Leu Leu Lys Lys Leu Arg Arg
                    5                   10                  15

(2) INFORMATION FOR SEQ ID NO:100:

(i) SEQUENCE CHARACTERISTICS:
        (A) LENGTH: 16 amino acids
        (B) TYPE: amino acid
        (C) STRANDEDNESS:
        (D) TOPOLOGY: linear (i i) MOLECULE TYPE: peptide (x i) SEQUENCE DESCRIPTION:SEQ ID NO:100:

Lys Leu Lys Lys Leu Leu Lys Lys Leu Lys
                    5                   10
Lys Leu Leu Lys Leu Leu
                15

(2) INFORMATION FOR SEQ ID NO:101:

(i) SEQUENCE CHARACTERISTICS:
        (A) LENGTH: 15 amino acids
        (B) TYPE: amino acid
        (C) STRANDEDNESS:
        (D) TOPOLOGY: linear (i i) MOLECULE TYPE: peptide (x i) SEQUENCE DESCRIPTION: SEQ ID NO:101:

Leu Lys Lys Leu Leu Lys Lys Leu Lys Lys
                    5                   10
Leu Leu Lys Lys Asn
                15

(2) INFORMATION FOR SEQ ID NO:102:

(i) SEQUENCE CHARACTERISTICS:
        (A) LENGTH: 15 amino acids
        (B) TYPE: amino acid
        (C) STRANDEDNESS:
        (D) TOPOLOGY: linear (i i) MOLECULE TYPE: peptide (i x) FEATURE:
        (D) OTHER INFORMATION: Xaa is homoserine.

(x i) SEQUENCE DESCRIPTION: SEQ ID NO:102:

Leu Lys Lys Leu Leu Lys Lys Leu Lys Lys
                    5                   10
Leu Leu Lys Lys Xaa
                15

(2) INFORMATION FOR SEQ ID NO:103:

(i) SEQUENCE CHARACTERISTICS:
        (A) LENGTH: 18 amino acids
        (B) TYPE: amino acid
        (C) STRANDEDNESS:
        (D) TOPOLOGY: linear (i i) MOLECULE TYPE: peptide (x i) SEQUENCE DESCRIPTION: SEQ ID NO:103:

```
Leu Lys Leu Leu Lys Lys Leu Leu Lys Lys
                 5                      10

Asn Lys Lys Leu Leu Lys Lys Leu
                15
```

( 2 ) INFORMATION FOR SEQ ID NO:104:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:104:

```
Leu Lys Leu Leu Lys Lys Leu Leu Lys Lys
                 5                      10

Pro Lys Lys Leu Leu Lys Lys Leu
                15
```

( 2 ) INFORMATION FOR SEQ ID NO:105:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:105:

```
Leu Leu Lys Lys Leu Lys Lys Leu Leu Lys
                 5                      10

Lys Leu Gln Gly Pro Pro Gln Gly Gln Ser
                15                      20

Pro Gln
```

( 2 ) INFORMATION FOR SEQ ID NO:106:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:106:

```
Leu Ala Ser Lys Ala Gly Ala Ile Ala Gly
                 5                      10

Lys Ile Ala Lys Lys Leu Leu Lys Lys Leu
                15                      20
```

( 2 ) INFORMATION FOR SEQ ID NO:107:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:107:

```
Leu Lys Lys Leu Lys Lys Leu
                 5
```

( 2 ) INFORMATION FOR SEQ ID NO:108:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:108:

Leu Leu Lys Lys Leu Lys Lys Leu
              5

( 2 ) INFORMATION FOR SEQ ID NO:109:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:109:

Lys Leu Leu Lys Lys Leu Lys Lys Leu
              5

( 2 ) INFORMATION FOR SEQ ID NO:110:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:110:

Lys Lys Leu Leu Lys Lys Leu Lys Lys Leu
              5                 10

( 2 ) INFORMATION FOR SEQ ID NO:111:

( i ) SEQUENCE CHARACTERISTICS:
        ( A ) LENGTH: 11 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:111:

Leu Lys Lys Leu Leu Lys Lys Leu Lys Lys Leu
              5                 10

( 2 ) INFORMATION FOR SEQ ID NO:112:

( i ) SEQUENCE CHARACTERISTICS:
        ( A ) LENGTH: 11 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:112:

Ala Lys Lys Leu Leu Lys Lys Leu Lys Lys Leu
              5                 10

( 2 ) INFORMATION FOR SEQ ID NO:113:

( i ) SEQUENCE CHARACTERISTICS:
  ( A ) LENGTH: 14 amino acids
  ( B ) TYPE: amino acid
  ( C ) STRANDEDNESS:
  ( D ) TOPOLOGY: linear ( i i ) MOLECULE TYPE: peptide ( x i ) SEQUENCE DESCRIPTION: SEQ ID NO:113:

Leu Lys Lys Leu Leu Lys Lys Leu Lys Lys Leu
                  5                          10

Leu Lys Arg ( 2 ) INFORMATION FOR SEQ ID NO:114:

( i ) SEQUENCE CHARACTERISTICS:
  ( A ) LENGTH: 26 amino acids
  ( B ) TYPE: amino acid
  ( C ) STRANDEDNESS:
  ( D ) TOPOLOGY: linear ( i i ) MOLECULE TYPE: peptide ( v i ) ORIGINAL SOURCE:
  ( A ) ORGANISM: Apis mellifera ( v i i ) FEATURE:
  ( A ) NAME/KEY: melittin peptide ( x ) PUBLICATION INFORMATION:
  ( A ) AUTHORS: Habermann, E.
                 Jentsch, J.
  ( B ) TITLE: Sequenzanalyse des Melittins aus
               den tryptischen and peptischen
               Spaltstucken
  ( C ) JOURNAL: Hoppe-Seyler's Zeitschrift
                 Physiol. Chem.
  ( D ) VOLUME: 348
  ( F ) PAGES: 37-50
  ( G ) DATE: 1987

( x i ) SEQUENCE DESCRIPTION: SEQ ID NO:114:

Gly Ile Gly Ala Val Leu Lys Val Leu
                 5

Thr Thr Gly Leu Pro Ala Leu Ile Ser Trp
10                   15

Ile Lys Arg Lys Arg Gln Gln
20                  25

( 2 ) INFORMATION FOR SEQ ID NO:115:

( i ) SEQUENCE CHARACTERISTICS:
  ( A ) LENGTH: 22 amino acids
  ( B ) TYPE: amino acid
  ( C ) STRANDEDNESS:
  ( D ) TOPOLOGY: linear ( i i ) MOLECULE TYPE: peptide ( x i ) SEQUENCE DESCRIPTION: SEQ ID NO:115:

Gly Ile Gly Lys Phe Leu Lys Lys Ala Lys
                 5                      10

Lys Phe Ala Lys Ala Phe Val Lys Ile Ile
                15                      20

Asn Asn (2) INFORMATION FOR SEQ ID NO:116:

(i) SEQUENCE CHARACTERISTICS:
        (A) LENGTH: 37 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Cecropin A (xi) SEQUENCE DESCRIPTION: SEQ ID NO:116:

```
Lys Trp Lys Leu Phe Lys Lys Ile Glu Lys
                 5                   10
Val Gly Gln Asn Ile Arg Asp Gly Ile Ile
                15                   20
Lys Ala Gly Pro Ala Val Ala Val Val Gly
                25                   30
Gln Ala Thr Gln Ile Ala Lys
                35
```

(2) INFORMATION FOR SEQ ID NO:117:

(i) SEQUENCE CHARACTERISTICS:
        (A) LENGTH: 22 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:117:

```
Gly Ile Gly Lys Phe Leu Lys Ser Ala Lys
                                     10
Lys Phe Gly Lys Ala Phe Val Lys Ile Leu
                15                   20
Asn Ser
```

TREATMENT OF GYNECOLOGICAL MALIGNANCIES WITH BIOLOGICALLY ACTIVE PEPTIDES

This application is a continuation, of application Ser. No. 08/297,950, now abandoned, filed Aug. 31, 1994, which is a continuation of Ser. No. 08/226,108, filed Apr. 11, 1994, now abandoned, which is a continuation of Ser. No. 07/937,462, filed Aug. 31, 1992, now abandoned.

This invention relates to the treatment of gynecological malignancies. More particularly, this invention relates to the treatment of gynecological malignancies by administering a biologically active peptide or protein.

In accordance with an aspect of the present invention, there is provided a process for treating a gynecological malignancy in a host comprising administering to a host at least one biologically active amphiphilic peptide or protein. The peptide or protein is an ion channel-forming peptide or protein. The peptide or protein is administered in an amount effective to treat a gynecological malignancy in a host.

The term "treating a gynecological malignancy" as used herein means that the peptide or protein prevents, inhibits, or destroys the growth of cancerous or malignant cells of a cancerous or malignant growth found in the female reproductive organs, such as, but not limited to, the ovaries, uterus, and cervix, and/or reduces the size of or eliminates the cancerous growth.

An ion channel-forming peptide or protein or ionophore is a peptide or protein which increases the permeability for ions across a natural or synthetic lipid membrane. B. Christensen, et al., PNAS, Vol. 85, pgs. 5072–5076 (July 1988) describes methodology which indicates whether or not a peptide has ion channel-forming properties and is therefore an ionophore. As used herein an ion channel-forming peptide or ion channel-forming protein is a peptide or protein which has ion channel-forming properties as determined by the method of Christensen, et al.

An amphiphilic peptide or protein is a peptide or protein which includes both hydrophobic and hydrophilic peptide or protein regions.

The ion channel-forming peptides employed in the present invention are generally water soluble to a concentration of at least 20 mg/ml at neutral pH in water. In addition, the structure of such peptide provides for flexibility of the peptide molecule. Such peptides are capable of forming an alpha-helix. When the peptide is placed in water, it does not assume an amphiphilic structure. When the peptide encounters an oily surface or membrane, the peptide chain folds upon itself into a rodlike structure.

In general, such peptides have at least 7 amino acids, and in many cases have at least 20 amino acids. In most cases, such peptides do not have in excess of 40 amino acids.

As stated hereinabove, the peptides or proteins are administered in an amount effective to treat gynecological malignancies in a host. The peptides or proteins may be administered to a host in vivo, such as, for example, through systemic administration, such as intravenous or intraperitoneal administration. Also, the peptides or proteins may be administered intralesionally; i.e., the peptide or protein is injected directly into the gynecological malignancy. The peptide or protein may be administered in an amount of from about 0.1 mg/kg to about 500 mg/kg, preferably, from about 1 mg/kg to about 100 mg/kg and more preferably from about 5 mg/kg to about 75 mg/kg. In one embodiment, the peptide or protein may be administered in an amount of from about 20 mg/kg to about 50 mg/kg given in one or two doses. In another embodiment, the peptide or protein may be administered in an amount of about 10 mg/kg per day intraperitoneally over a five day period.

The peptides or proteins administered in combination with an acceptable pharmaceutical carrier or vehicle such as a filler, non-toxic buffer, or physiological saline solution. The peptides or proteins may also be used in combination with adjuvants, protease inhibitors, or compatible drugs.

Gynecological malignancies which may be treated with the peptides or proteins of the present invention include, but are not limited to, ovarian cancers, uterine cancers, and cervical cancers. Ovarian cancers which may be treated include, but are not limited to, primary ovarian cancers including Stage 1 and Stage 1C or greater as classified by the International Federation of Gynecology and Obstetrics. Stage 1 is when tumor growth is limited to one or both ovaries. Stage 1C includes a stage of development of ovarian cancer in which ascites and positive tumor cells are found in peritoneal washes.

In one embodiment, the peptide is a basic (positively charged) polypeptide having at least sixteen amino acids wherein the polypeptide includes at least eight hydrophobic amino acids and at least eight hydrophilic amino acids. Still more particularly, the hydrophobic amino acids are in groups of two adjacent amino acids, and each group of two hydrophobic amino acids is spaced from another group of two hydrophobic amino acids by at least one amino acid other than a hydrophobic amino acid (preferably at least two amino acids) and generally by no greater than four amino acids, and the amino acids between pairs of hydrophobic amino acids may or may not be hydrophilic.

The hydrophilic amino acids are generally also in groups of two adjacent amino acids in which at least one of the two amino acids is a basic hydrophilic amino acid, with such groups of two hydrophilic amino acids being spaced from each other by at least one amino acid other than a hydrophilic amino acid (preferably at least two amino acids) and generally no greater then four amino acids, and the amino acids between pairs of hydrophilic amino acids may or may not be hydrophobic.

In accordance with a particularly preferred embodiment, the polypeptide comprises a chain of at least four groups of amino acids, with each group consisting of four amino acids. Two of the four amino acids in each group are hydrophobic amino acids, and two of the four amino acids in each group are hydrophilic, with at least one of the hydrophilic amino acids In each group being a basic hydrophilic amino acid and the other being a basic or neutral hydrophilic amino acid.

The hydrophobic amino acids may be selected from the class consisting of Ala, Cys, Phe, Gly, Ile, Leu, Met, Pro, Val, Trp, Tyr, norleucine (Nle), norvaline (Nva), and cyclohexylalanine (Cha). The neutral hydrophilic amino acids may be selected from the class consisting of Asn, Gln, Ser, Thr and homoserine (Hse). The basic hydrophilic amino acids may be selected from the class consisting of Lys, Arg, His, Orn, homoarginine (Har), 2, 4-diaminobutyric acid (Dbu), and p-aminophenylalanine.

Each of the groups of four amino acids may be of the sequence ABCD, BCDA, CDAB, or DABC, wherein A and B are each hydrophobic amino acids and may be the same or different, one of C or D is a basic hydrophilic amino acid, and the other of C or D is a basic or neutral hydrophilic amino acid and may be the same or different. In one embodiment, the polypeptide chin may comprise 5 or 6 groups of this sequence. In each group, each of A, B, C and D may be the same in some or all of the groups or may be different in some or all of the groups.

The polypeptide chain preferably has at least 20 amino acids, and no greater than 50 amino acids. It is to be understood, however, that the polypeptide does not have to consist entirely of the groups described above. The polypeptide may have amino acids extending from either or both ends of the noted groups forming the polypeptide chain and/or there may be amino acids between one or more of the at least four groups and still remain within the scope of the invention.

The groups of amino acids may be repeating groups of amino acids, or the amino acids in the various groups may vary provided that in each group of the at least four groups of amino acids there are two hydrophobic and two hydrophilic amino acids as hereinabove noted.

Thus the biologically active polypeptide may comprise a chain including at least four groups of amino acids, each containing four amino acids. Two of the four amino acids in each group are hydrophobic, at least one amino acid is basic hydrophilic, and the remaining one is basic or neutral hydrophilic, with the polypeptide chain preferably having at least 20 amino acids but no greater than 50 amino acids.

In one embodiment, each of the at least four groups of amino acids which are in the peptide chain is of the sequence A-B-C-D, B-C-D-A, C-D-A-B or D-A-B-C wherein A and B are hydrophobic amino acids, one of C or D is a basic hydrophilic amino acid, and the other of C or D is basic or neutral hydrophilic amino acid. The resulting polypeptide chain, therefore, may have one of the following sequences:

$$(X_1)_a(A\text{-}B\text{-}C\text{-}D)_n(Y_1)_b$$

$$(X_2)_a(B\text{-}C\text{-}D\text{-}A)_n(Y_2)_b$$

$$(X_3)_a(C\text{-}D\text{-}A\text{-}B)_n(Y_3)_b$$

$$(X_4)_a(D\text{-}A\text{-}B\text{-}C)_n(Y_4)_b$$

wherein $X_1$ is D; C-D- or B-C-D-, $Y_1$ is -A or -A-B or -A-B-C $X_2$ is A-, D-A- or C-D-A-

$Y_2$ is -B, -B-C or B-C-D $X_3$ is B-, A-B-, D-A-B-

$Y_3$ is -C, -C-D, -C-D-A $X_4$ is C-, B-C-, A-B-C-

$Y_4$ is -D, -D-A, -D-A-B a is 0 or 1; b is 0 or 1 and n is at least 4.

It is to be understood that the peptide chain may include amino acids between the hereinabove noted groups of four amino acids provided that the spacing between such groups and the charge on the amino acids does not change the characteristics of the peptide chain which provide amphiphilicity and a positive charge and do not adversely affect the folding characteristics of the chain to that which is significantly different from one in which the hereinabove noted group of four amino acids are not spaced from each other.

As representative examples of such peptides, there may be mentioned.

I Ala-Phe-Ser-Lys-Ala-Phe-Ser-Lys-Ala-Phe-Ser-Lys-Ala-Phe-Ser-Lys-Ala-Phe-Ser-Lys (SEQ ID NO:1)

II Ala-Phe-Ser-Lys-Ala-Phe-Ser-Lys-Ala-Phe-Ser-Lys-Ala-Phe-Ser-Lys-Ala-Phe-Ser-Lys-Ala-Phe-Ser-Lys. (SEQ ID NO:2)

III Phe-Ser-Lys-Ala-Phe-Ser-Lys-Ala-Phe-Ser-Lys-Ala-Phe-Ser-Lys-Ala- (SEQ ID NO:3)

IV Ser-Lys-Ala-Phe-Ser-Lys-Ala-Phe-Ser-Lys-Ala-Phe-Ser-Lys-Ala-Phe-Ser-Lys-Ala-Phe- (SEQ ID NO:4)

V Lys-Ala-Phe-Ser-Lys-Ala-Phe-Ser-Lys-Ala-Phe-Ser-Lys-Ala-Phe-Ser (SEQ ID NO:5)

The peptide may have amino acids extending from either end of the chain. For example, the chains may have a Ser-Lys sequence before the "Ala" end, and/or an Ala-Phe sequence after the "Lys" end. Other amino acid sequences may also be attached to the "Ala" and/or the "Lys" end.

Similarly, in any polypeptide chain having at least four groups of amino acids of the sequence as described above, the chain may have, for example, a C-D sequence before the first A-B-C-D group. Also other amino acid sequences may be attached to the "A" and/or the "D" end of one of these polypeptide chains. Also there may be amino acids in the chain which space one or more groups of the hereinabove noted four amino acids from each other.

In accordance with another embodiment, the peptide may be a magainin peptide.

A magainin peptide is either a magainin such as magainin I, II or III or an analogue or derivative thereof. The magainin peptides preferably include the following basic peptide structure $X_{12}$:

$$\text{-}R_{11}\text{-}R_{11}\text{-}R_{12}\text{-}R_{13}\text{-}R_{11}\text{-}R_{14}\text{-}R_{12}\text{-}R_{11}\text{-}R_{14}\text{-}R_{12}\text{-}R_{11}\text{-}R_{11}\text{-}R_{11}\text{-}R_{11}\text{-}R_{14a}\text{-}(R_{15})_n\text{-}R_{14a}\text{-}R_{14}$$

wherein $R_{11}$ is a hydrophobic amino acid, $R_{12}$ is a basic hydrophilic amino acid; $R_{13}$ is a hydrophobic, neutral hydrophilic, or basic hydrophilic amino acid; $R_{14}$ and $R_{14a}$ are hydrophobic or basic hydrophilic amino acids; $R_{15}$ is glutamic acid or aspartic acid, or a hydrophobic or a basic hydrophilic amino acid, and n is 0 or 1. In a preferred embodiment, $R_{13}$ is a hydrophobic or neutral hydrophilic amino acid, $R_{14a}$ is a hydrophobic amino acid, and $R_{15}$ is glutamic acid or aspartic acid.

Thus, for example, a magainin peptide may include the following structure:

$$\text{-}Y_{12}\text{-}X_{12}\text{-}$$

where $X_{12}$ is the hereinabove described basic peptide structure and $Y_{12}$ is (i) $R_{12}$ (ii) $R_{14a}\text{-}R_{12}$ (iii) $R_{11}\text{-}R_{14a}\text{-}R_{12}$ (iv) $R_{14}\text{-}R_{11}\text{-}R_{14a}\text{-}R_{12}$ where $R_{11}$, $R_{12}$, $R_{14}$ and $R_{14a}$ are as previously defined.

A magainin peptide may also have the following structure:

$$\text{-}X_{12}\text{-}Z_{12}\text{-}$$

wherein $X_{12}$ is as previously defined and $Z_{12}$ is:

(i) $R_{16}$ where $R_{16}$ is a basic hydrophilic amino acid or asparagine or glutamine.

(ii) $R_{16}\text{-}R_{17}$ where $R_{17}$ is a neutral hydrophilic amino acid, a hydrophobic amino acid, or a basic hydrophilic amino acid. Preferably, $R_{17}$ is a neutral hydrophilic amino acid.

A magainin peptide may also have the following structure:

$$(Y_{12})_a\text{-}X_{12}\text{-}(Z_{12})_b$$

where $X_{12}$, $Y_{12}$ and $Z_{12}$ are as previously defined and a is 0 or 1 and b is 0 or 1.

The magainin peptides may also include the following basic peptide structure $X_{13}$:

$\text{-}R_{14}\text{-}R_{11}\text{-}R_{14a}\text{-}R_{12}\text{-}R_{11}\text{-}R_{11}\text{-}R_{12}\text{-}R_{13}\text{-}R_{11}\text{-}R_{14}\text{-}R_{12}\text{-}R_{11}\text{-}R_{11}\text{-}R_{12}\text{-}$, wherein $R_{11}$, $R_{12}$, $R_{13}$, $R_{14}$, and $R_{14a}$ are amino acids as hereinabove described.

The magainin peptide may also include the following structure $X_3$-$Z_{13}$; wherein $X_{13}$ is the hereinabove described basic peptide structure and $Z_{13}$ is $(R_{11})_n$-$(R_{11})_n$-$(R_{11})_n$-$(R_{14a})_n$-$(R_{15})_n$-$(R_{14a})_n$-$(R_{14})_n$-$(R_{16})_n$-$(R_{17})_n$ wherein $R_{11}$, $R_{14}$, $R_{14a}$, $R_{15}$, $R_{16}$, and $R_{17}$ are as hereinabove described, and n is 0 or 1, end each n may be the same or different.

The magainin peptides generally include at least fourteen amino acids and may include up to forty amino acids. A magainin peptide preferably has 22 or 23 amino acids. Accordingly, the hereinabove described basic peptide structures of a magainin peptide may include additional amino acids at the amino end or at the carboxyl end, or at both ends.

As representative examples of such magainin peptides, there may be mentioned peptides having the following primary sequences as given in the accompanying sequence listing as well as appropriate analogues and derivatives thereof:

(a) (SEQ ID NO:6) (OH) or (NH$_2$) (Magainin I)
(b) (SEQ ID NO:7) (OH) or (NH$_2$) (Magainin II)
(c) (SEQ ID NO:8) (OH) or (NH$_2$) (Magainin III)

The following are examples of peptide derivatives or analogs of the basic structure:

(d) (SEQ ID NO:9) (OH) or (NH$_2$)
(e) (SEQ ID NO:10) (OH) or (NH$_2$)
(f) (SEQ ID NO: $_{11}$) (OH) or (NH$_2$)

Magainin peptides are described in *Proc. Natl. Acad. Sci.* Vol. 84 pp. 5449–53 (Aug. 87). The term "magainin peptides" as used herein refers to the basic magainin structure as well as derivatives and analogs thereof, including but not limited to the representative derivatives or analogs.

In accordance with a further embodiment, the peptide may be a PGLa peptide or an XPF peptide.

A PGLa peptide is either PGLa or an analogue or derivative thereof. The PGLa peptides preferably include the following basic peptide structure $X_{14}$:

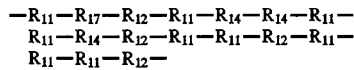

where $R_{11}$, $R_{12}$, $R_{14}$, and $R_{17}$ are as previously defined.

The PGLa peptides generally include at least seventeen amino acids and may include as many as forty amino acids. Accordingly, the hereinabove described basic peptide structure for a PGLa peptide may include additional amino acids at the amino end or at the carboxyl end or at both the amino and carboxyl end.

Thus, for example, a PGLa peptide may have the following structure:

where $X_{14}$ is as previously defined and $Y_{14}$ is
(i) $R_{11}$;
(ii) $R_{14}$-$R_{11}$
where $R_{11}$ and $R_{14}$ are as previously defined.

For example, a PGLa peptide may also have the following structure:

where $X_{14}$ is as previously defined; and $Z_{14}$ is:
(i) $R_{11}$; or
(ii) $R_{11}$-$R_{11}$
where $R_{11}$ is as previously defined.

A PGLa peptide may also have the following structure:

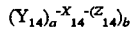

where $X_{14}$; $Y_{14}$ and $Z_{14}$ are as previously defined, a is 0 or 1 and b is 0 or 1.

An XPF peptide is either XPF or an analogue or derivative thereof. The XPF peptides preferably include the following basic peptide structure $X_{16}$:

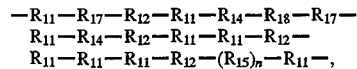

wherein
$R_{11}$, $R_{12}$, $R_{14}$, $R_{15}$ and $R_{17}$ are as previously defined and $R_{18}$ is glutamine or asparagine or a basic hydrophilic, or hydrophobic amino acid and, n is 0 or 1.

The XPF peptides generally include at least nineteen amino acids and may include up to forty amino acids. Accordingly, the hereinabove described basic peptide structure of XPF may include additional amino acids at the amino end, or at the carboxyl end or at both the amino and carboxyl ends.

Thus, for example, an XPF peptide may include the following structure:

where $X_{16}$ is as previously defined and $Y_{16}$ is
(i) $R_{11}$ or
(ii) $R_{14}$-$R_{11}$
where $R_{11}$ and $R_{14}$ are as previously defined.

An XPF peptide may include the following structure:

where $X_{16}$ is as previously defined and $Z_{16}$ is
(i) $R_{11}$; or
(ii) $R_{11}$-$R_{18}$; or
(iii) $R_{11}$-$R_{18}$-Proline; or
(iv) $R_{11}$-$R_{18}$-Proline-$R_{12}$ An XPF peptide may also have the following structure:

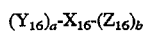

where $X_{16}$, $Y_{16}$ and $Z_{16}$ are as previously defined: a is 0 or 1 and b is 0 or 1.

Preferred are XPF or PGLa peptides, which are characterized by the following primary amino acid sequences as given in the accompanying sequence listing:

PGLa: (SEQ ID NO:12) (NH$_2$)
XPF : (SEQ ID NO:13)

A review of XPF and PGLa can be found in Hoffman et al, *EMBO J.* 2:711–714, 1983; Andreu, et al, *J. Biochem.* 531–535, 1985; Gibson, et al *J. Biol. Chem.* 5341–5349, 1986; and Giovannini, et al, *Biochem J.* 243:113–120, 1987.

In accordance with yet another embodiment, the peptide may be a CPF peptide or appropriate analogue or derivative thereof.

CPF peptides as well as analogues and derivatives thereof are herein sometimes referred to collectively as CPF peptides.

The CPF peptide may be one which includes the following basic peptide structure $X_{20}$:

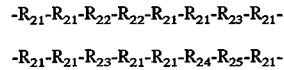

wherein
$R_{21}$ is a hydrophobic amino acid;

$R_{22}$ is a hydrophobic amino acid or a basic hydrophilic amino acid;

$R_{23}$ is a basic hydrophilic amino acid;

$R_{24}$ is a hydrophobic or neutral hydrophilic amino acid; and $R_{25}$ is a basic or neutral hydrophilic amino acid.

The hereinabove basic structure is hereinafter symbolically indicated as $X_{20}$.

The hydrophobic amino acids are Ala, Cys, Phe, Gly, Ile, Leu, Met, Val, Trp, Tyr, norleucine (Nle), norvaline (Nva), and cyclohexylalanine (Cha).

The neutral hydrophilic amino acids are Asn, Gln, Ser, Thr, and homoserine (Hse).

The basic hydrophilic amino acids are Lys, Arg, His, Orn, homoarginine (Har), 2,4-diaminobutyric acid (Dbu), and p-aminophenylalanine.

The CPF peptide may include only the hereinabove noted amino acids or may include additional amino acids at the amino and/or carboxyl end or both the amino and carboxyl end. In general, the peptide does not include more than 40 amino acids.

The CPF peptides including the above basic structure preferably have from 1 to 4 additional amino acids at the amino end.

Accordingly, such preferred peptides may be represented by the structural formula:

$$Y_{20}\text{-}X_{20}\text{-}$$

wherein $X_{20}$ is the hereinabove described basic peptide structure and $Y_{20}$ is (i) $R_{25}$-, or (ii) $R_{22}$-$R_{25}$-; or (iii) $R_{21}$-$R_{22}$-$R_{25}$; or (iv) $R_{22}$-$R_{21}$-$R_{22}$-$R_{25}$; preferably Glycine-$R_{21}$-$R_{22}$-$R_{25}$. wherein $R_{21}$, $R_{22}$ end $R_{25}$ are as previously defined.

The carboxyl end of the basic peptide structure may also have additional amino acids which may range from 1 to 13 additional amino acids.

In a preferred embodiment, the basic structure may have from 1 to 7 additional amino acids at the carboxyl end, which may be represented as follows:

$$\text{-}X_{20}\text{-}Z_{20}$$

wherein X is the hereinabove defined basic peptide structure and $Z_{20}$ is (i) $R_{21}$-, or (ii) $R_{21}$-$R_{21}$-; or (iii) $R_{21}$-$R_{21}$-$R_{24}$; or (iv) $R_{21}$-$R_{21}$-$R_{24}$-$R_{24}$; or (v) $R_{21}$-$R_{21}$-$R_{24}$-$R_{24}$-$R_{26}$; or (vi) $R_{21}$-$R_{21}$-$R_{24}$-$R_{24}$-$R_{26}$-Gln; or (vii) $R_{21}$-$R_{21}$-$R_{24}$-$R_{24}$-$R_{26}$-Gln-Gln, wherein $R_{21}$ and $R_{24}$ are as previously defined, and $R_{26}$ is proline or a hydrophobic amino acid.

Preferred peptides may be represented by the following structural formula $$(Y_{20})_a\text{-}X_{20}\text{-}(Z_{20})_b$$

wherein $X_{20}$, $Y_{20}$ and $Z_{20}$ are as previously defined and a is 0 or 1 and b is 0 or 1.

Representative examples of CPF peptides which may be employed, some of which have been described in the literature, include the following sequences as given in the accompanying sequence listing:

(SEQ ID NO:14)
(SEQ ID NO:15)
(SEQ ID NO:16)
(SEQ ID NO:17)
(SEQ ID NO:18)
(SEQ ID NO:19)
(SEQ ID NO:20)
(SEQ ID NO:21)
(SEQ ID NO:22)
(SEQ ID NO:23)
(SEQ ID NO:24)
(SEQ ID NO:25)
(SEQ ID NO:26)

A review of the CPF peptides can be found in Richter, K., Egger, R., and Kreil (1986) *J. Biol. Chem* 261, 3676–3680; Wakabayashi, T., Kato, H., and Tachibaba, S. (1985) Nucleic Acids Research 13, 1817–1828; Gibson, B. W., Poulter, L., Williams, D. H., and Maggio, J. E. (1986) *J. Biol. Chem* 261, 5341–5349.

In accordance with yet another embodiment, the peptide may include one of the following basic structures $X_{31}$ through $X_{37}$ wherein:

$X_{31}$ is -$[R_{31}$-$R_{32}$-$R_{32}$-$R_{33}$-$R_{31}$-$R_{32}$-$R_{32}]$-$_n$;

$X_{32}$ is -$[R_{32}$-$R_{32}$-$R_{33}$-$R_{31}$-$R_{32}$-$R_{32}$-$R_{31}]$-$_n$;

$X_{33}$ is -$[R_{32}$-$R_{33}$-$R_{31}$-$R_{32}$-$R_{32}$-$R_{31}$-$R_{32}]$-$_n$;

$X_{34}$ is -$[R_{33}$-$R_{31}$-$R_{32}$-$R_{32}$-$R_{31}$-$R_{32}$-$R_{32}]$-$_n$;

$X_{35}$ is -$[R_{31}$-$R_{32}$-$R_{32}$-$R_{31}$-$R_{32}$-$R_{32}$-$R_{33}]$-$_n$;

$X_{36}$ is -$[R_{32}$-$R_{32}$-$R_{31}$-$R_{32}$-$R_{32}$-$R_{33}$-$R_{31}]$-$_n$; and $X_{37}$ is -$[R_{32}$-$R_{31}$-$R_{32}$-$R_{32}$-$R_{33}$-$R_{31}$-$R_{32}]$-$_n$;

wherein $R_{31}$ is a basic hydrophilic amino acid, $R_{32}$ is a hydrophobic amino acid, $R_{33}$ is a neutral hydrophilic, basic hydrophilic, or hydrophobic amino acid, and n is from 2 to 5.

The basic hydrophilic amino acids may be selected from the class consisting of Lys, Arg, His, Orn, homoarginine (Har), 2,4-diaminobutyric acid (Dbu), and p-aminophenylalanine.

The hydrophobic amino acids may be selected from the class consisting of Ala, Cys, Phe, Gly, Ile, Leu, Met, Pro, Val, Trp and Tyr, norleucine (Nle), norvaline (Nva), and cyclohexylalanine (Cha).

The neutral hydrophilic amino acids may be selected from the class consisting of Asn, Gln, Set, Thr, and homoserine (Hse).

In accordance with one embodiment, when the peptide includes the structure $X_{31}$, the peptide may include the following structure:

$$Y_{31}\text{-}X_{31},$$

wherein $X_{31}$ is as hereinabove described, and $Y_{31}$ is:

(i) $R_{32}$;

(ii) $R_{32}$-$R_{32}$;

(iii) $R_{31}$-$R_{32}$-$R_{32}$;

(iv) $R_{33}$-$R_{31}$-$R_{32}$-$R_{32}$;

(v) $R_{32}$-$R_{33}$-$R_{31}$-$R_{32}$-$R_{32}$; or (vi) $R_{32}$-$R_{32}$-$R_{33}$-$R_{31}$-$R_{32}$-$R_{32}$, wherein $R_{31}$, $R_{32}$, and $R_{33}$ are as hereinabove described.

In accordance with another embodiment, when the peptide includes the structure $X_{31}$, the peptide may include the following structure:

$$X_{31}\text{-}Z_{31},$$

wherein $X_{31}$ is as hereinabove described, and $Z_{31}$ is:

(i) $R_{31}$;
(ii) $R_{31}$-$R_{32}$;
(iii) $R_{31}$-$R_{32}$-$R_{32}$;
(iv) $R_{31}$-$R_{32}$-$R_{32}$-$R_{33}$;
(v) $R_{31}$-$R_{32}$-$R_{32}$-$R_{33}$-$R_{31}$; or
(vi) $R_{31}$-$R_{32}$-$R_{32}$-$R_{33}$-$R_{31}$-$R_{32}$.

In accordance with yet another embodiment, the peptide may include the following structure:

$$(Y_{31})_a\text{-}X_{31}\text{-}(Z_{31})_b,$$

wherein $Y_{31}$ and $Z_{31}$ are as previously defined, a is 0 or 1, and b is 0 or 1.

When the peptide includes the structure $X_{32}$, the peptide may include the following structure:

$$Y_{32},$$

wherein $X_{32}$ is as hereinabove described, and $Y_{32}$ is:
(i) $R_{31}$;
(ii) $R_{32}$-$R_{31}$;
(iii) $R_{32}$-$R_{32}$-$R_{31}$;
(iv) $R_{31}$-$R_{32}$-$R_{32}$-$R_{31}$;
(v) $R_{33}$-$R_{31}$-$R_{32}$-$R_{32}$-$R_{31}$; or
(vi) $R_{32}$-$R_{33}$-$R_{31}$-$R_{32}$-$R_{32}$-$R_{31}$.

In another embodiment, when the peptide includes the structure $X_{32}$, the peptide may include the following structure:

$$X_{32}\text{-}Z_{32},$$

wherein $X_{32}$ is as hereinabove described, and $Z_{32}$ is:
(i) $R_{32}$;
(ii) $R_{32}$-$R_{32}$;
(iii) $R_{32}$-$R_{32}$-$R_{33}$;
(iv) $R_{32}$-$R_{32}$-$R_{33}$-$R_{31}$;
(v) $R_{32}$-$R_{32}$-$R_{33}$-$R_{31}$-$R_{32}$; or
(vi) $R_{32}$-$R_{32}$-$R_{33}$-$R_{31}$-$R_{32}$-$R_{32}$.

In accordance with yet another embodiment, the peptide may include the following structure:

$$(Y_{32})_a\text{-}X_{32}\text{-}(Z_{32})_b,$$

wherein $Y_{32}$ and $Z_{32}$ are as previously defined, a is 0 or 1, and b is 0 or 1.

In accordance with another embodiment, when the peptide includes the structure $X_{33}$, the peptide may include the following structure:

$$Y_{33}\text{-}X_{33}$$

wherein $X_{33}$ is as hereinabove described, and $Y_{33}$ is:
(i) $R_{32}$;
(ii) $R_{31}$-$R_{32}$;
(iii) $R_{32}$-$R_{31}$-$R_{32}$;
(iv) $R_{32}$-$R_{32}$-$R_{31}$-$R_{32}$;
(v) $R_{31}$-$R_{32}$-$R_{32}$-$R_{31}$-$R_{32}$; or
(vi) $R_{33}$-$R_{31}$-$R_{32}$-$R_{32}$-$R_{31}$-$R_{32}$, wherein $R_{31}$, $R_{32}$, and $R_{33}$ are as hereinabove described.

In accordance with another embodiment, when the peptide includes the structure $X_{33}$, the peptide may include the following structure:

$$X_{33}\text{-}Z_{33}$$

wherein $X_{33}$ is as hereinabove described, and $Z_{33}$ is:
(i) $R_{32}$;
(ii) $R_{32}$-$R_{33}$;
(iii) $R_{32}$-$R_{33}$-$R_{31}$;
(iv) $R_{32}$-$R_{33}$-$R_{31}$-$R_{32}$;
(v) $R_{32}$-$R_{33}$-$R_{31}$-$R_{32}$-$R_{32}$; or
(vi) $R_{32}$-$R_{33}$-$R_{31}$-$R_{32}$-$R_{32}$-$R_{31}$.

In accordance with yet another embodiment, the peptide may include the following structure:

$$(Y_{33})_a\text{-}X_{33}\text{-}(Z_{33})_b,$$

wherein $Y_{33}$ end $Z_{33}$ are as previously defined, a is 0 or 1, and b is 0 or 1.

In accordance with yet another embodiment, when the peptide includes the structure $X_{34}$, the peptide may include the following structure:

$$Y_{34}\text{-}X_{34},$$

wherein $X_{34}$ is as hereinabove described, and $Y_{34}$ is:
(i) $R_{32}$;
(ii) $R_{32}$-$R_{32}$;
(iii) $R_{31}$-$R_{32}$-$R_{32}$;
(iv) $R_{32}$-$R_{31}$-$R_{32}$-$R_{32}$;
(v) $R_{32}$-$R_{32}$-$R_{31}$-$R_{32}$-$R_{32}$; or
(vi) $R_{31}$-$R_{32}$-$R_{32}$-$R_{31}$-$R_{32}$-$R_{32}$, wherein $R_{31}$, $R_{32}$ and $R_{33}$ are as hereinabove described.

In accordance with another embodiment, when the peptide includes the structure $X_{34}$, the peptide may include the following structure:

$$X_{34}\text{-}Z_{34},$$

wherein $X_{34}$ is as hereinabove described, and $Z_{34}$ is:
(i) $R_{33}$;
(ii) $R_{33}$-$R_{31}$;
(iii) $R_{33}$-$R_{31}$-$R_{32}$;
(iv) $R_{33}$-$R_{31}$-$R_{32}$-$R_{32}$;
(v) $R_{33}$-$R_{31}$-$R_{32}$-$R_{32}$-$R_{31}$; or
(vi) $R_{33}$-$R_{31}$-$R_{32}$-$R_{32}$-$R_{31}$-$R_{32}$.

In accordance with yet another embodiment, the peptide may include the following structure:

$$(Y_{34})_a\text{-}X_{34}\text{-}(Z_{34})_b,$$

wherein $X_{34}$ and $Z_{34}$ are as previously defined, a is 0 or 1, and b is 0 or 1.

In accordance with a further embodiment, when the peptide includes the structure $X_{35}$, the peptide may include the following structure:

$$Y_{35}\text{-}X_{35},$$

wherein $X_{35}$ is as hereinabove described, and $Y_{35}$ is:
(i) $R_{33}$;
(ii) $R_{32}$-$R_{33}$;
(iii) $R_{32}$-$R_{32}$-$R_{33}$;
(iv) $R_{31}$-$R_{32}$-$R_{32}$-$R_{33}$;
(v) $R_{32}$-$R_{31}$-$R_{32}$-$R_{32}$-$R_{33}$; or
(vi) $R_{32}$-$R_{32}$-$R_{31}$-$R_{32}$-$R_{32}$-$R_{33}$, wherein $R_{31}$, $R_{32}$, and $R_{33}$ are as hereinabove described.

In accordance with another embodiment, when the peptide includes the structure $X_{35}$, the peptide may include the following structure:

$$X_{35}\text{-}Z_{35}$$

wherein $X_{35}$ is as hereinabove described, and $Z_{35}$ is:
(i) $R_{31}$;
(ii) $R_{31}$-$R_{32}$;
(iii) $R_{31}$-$R_{32}$-$R_{32}$;
(iv) $R_{31}$-$R_{32}$-$R_{32}$-$R_{31}$;
(v) $R_{31}$-$R_{32}$-$R_{32}$-$R_{31}$-$R_{32}$; or
(vi) $R_{31}$-$R_{32}$-$R_{32}$-$R_{31}$-$R_{32}$-$R_{32}$.

In accordance with yet another embodiment, the peptide may include the following structure:

$$(Y_{35})_a\text{-}X_{35}(Z_{35})_b,$$

wherein $X_{35}$ and $Z_{35}$ are as previously defined, a is 0 or 1, and b is 0 or 1.

In accordance with a further embodiment, when the peptide includes the structure $X_{36}$, the peptide may include the following structure:

$$Y_{36}\text{-}X_{36}$$

wherein $X_{36}$ is as hereinabove described, and $Y_{36}$ is:
(i) $R_{31}$;
(ii) $R_{33}$-$R_{31}$;
(iii) $R_{32}$-$R_{33}$-$R_{31}$;
(iv) $R_{32}$-$R_{32}$-$R_{33}$-$R_{31}$;
(v) $R_{31}$-$R_{32}$-$R_{32}$-$R_{33}$-$R_{31}$; or
(vi) $R_{32}$-$R_{31}$-$R_{32}$-$R_{32}$-$R_{33}$-$R_{31}$, wherein $R_3$, $R_{32}$, and $R_{33}$ are as hereinabove described.

In accordance with another embodiment, when the peptide includes the structure $X_{36}$, the peptide may include the following structure:

$$X_{36}\text{-}Z_{36},$$

wherein $X_{36}$ is as hereinabove described, and $Z_{36}$ is:
(i) $R_{32}$;
(ii) $R_{32}$-$R_{32}$;
(iii) $R_{32}$-$R_{32}$-$R_{31}$;
(iv) $R_{32}$-$R_{32}$-$R_{31}$-$R_{32}$;
(v) $R_{32}$-$R_{32}$-$R_{31}$-$R_{32}$-$R_{32}$; or
(vi) $R_{32}$-$R_{32}$-$R_{31}$-$R_{32}$-$R_{32}$-$R_{33}$.

In accordance with yet another embodiment, the peptide may include the following structure:

$$(Y_{36})_a\text{-}X_{36}(Z_{36})_b,$$

wherein $Y_{36}$ and $Z_{36}$ are as previously defined, a is 0 or 1, end b is 0 or 1.

In accordance with one embodiment, when the peptide includes the structure $X_{37}$, the peptide may includes the structure $Y_{37}$-$X_{37}$, wherein $X_{37}$ is as hereinabove described, and $Y_{37}$ is:
(i) $R_{32}$;
(ii) $R_{31}$-$R_{32}$;
(iii) $R_{33}$-$R_{31}$-$R_{32}$;
(iv) $R_{32}$-$R_{33}$-$R_{31}$-$R_{32}$;
(v) $R_{32}$-$R_{32}$-$R_{33}$-$R_{31}$-$R_{32}$; or
(vi) $R_{31}$-$R_{32}$-$R_{32}$-$R_{33}$-$R_{31}$-$R_{32}$, wherein $R_{31}$, $R_{32}$, and $R_{33}$ are as hereinabove described.

In accordance with a further embodiment, when the peptide includes the structure $X_{37}$, the peptide may include the following structure:

$$X_{37}\text{-}Z_{37}$$

wherein $X_{37}$ is as hereinabove described, and $Z_{37}$ is:
(i) $R_{32}$;
(ii) $R_{32}$-$R_{31}$;
(iii) $R_{32}$-$R_{31}$-$R_{32}$;
(iv) $R_{32}$-$R_{31}$-$R_{32}$-$R_{32}$;
(v) $R_{32}$-$R_{31}$-$R_{32}$-$R_{32}$-$R_{33}$; or
(vi) $R_{32}$-$R_{31}$-$R_{32}$-$R_{32}$-$R_{33}$-$R_{31}$.

In accordance with yet another embodiment, the peptide may include the following structure:

$$(Y_{37})_a\text{-}X_{37}(Z_{37})_b,$$

wherein $Y_{37}$ and $Z_{37}$ are as previously defined, a is 0 or 1, and b is 0 or 1.

In a preferred embodiment, n is 3, and most preferably the peptide is of one of the following structures as given in the accompanying sequence listing:

(Lys Ile Ala Gly Lys Ile Ala)$_3$ (SEQ ID NO:27).
(Lys Ile Ala Lys Ile Ala Gly)$_3$ (SEQ ID NO:28).
(Lys Ile Ala Gly Lys Ile Gly)$_3$ (SEQ ID NO:29).
(Lys Leu Ala Gly Lys Leu Ala)$_3$ (SEQ ID NO:30).
(Lys Phe Ala Gly Lys Phe Ala)$_3$ (SEQ ID NO:31).
(Lys Ala Leu Set Lys Ala Leu)$_3$ (SEQ ID NO:32).
(Lys Leu Leu Lys Ala Leu Gly)$_3$ (SEQ ID NO:33).
(Lys Ala lie Gly Lys Ala Ile)$_3$ (SEQ ID NO:34).
(Gly Ile Ala Lys Ile Ala Lys)$_3$ (SEQ ID NO:35).
(Lys Ile Ala Lys Ile Phe Gly)$_3$ (SEQ ID NO:36).
(Gly Ile Ala Arg Ile Ala Lys)$_3$ (SEQ ID NO:37).
(Lys Phe Ala Arg Ile Ala Gly)$_3$ (SEQ ID NO:38).
(Gly Phe Ala Lys Ile Ala Lys)$_3$ (SEQ ID NO:39).
(Lys Ile Ala Gly Orn Ile Ala)$_3$ (SEQ ID NO:40).
(Lys Ile Ala Arg Ile Ala Gly)$_3$ (SEQ ID NO:41).
(Orn Ile Ala Gly Lys Ile Ala)$_3$ (SEQ ID NO:42).
(Gly Ile Ala Arg Ile Phe Lys)$_3$ (SEQ ID NO:43).
(Lys Nle Ala Gly Lys Nle Ala)$_3$ (SEQ ID NO:44).
(Lys Nle Ala Gly Lys Ile Ala)$_3$ (SEQ ID NO:45).
(Lys Ile Ala Gly Lys Nle Ala)$_3$ (SEQ ID NO:46).
(Lys Nva Ala Gly Lys Nva Ala)$_3$ (SEQ ID NO:47).
(Lys Nva Ala Gly Lys Ile Ala)$_3$ (SEQ ID NO:48).
(Lys Leu Leu Set Lys Leu Gly)$_3$ (SEQ ID NO:49).
(Lys Leu Leu Ser Lys Phe Gly)$_3$ (SEQ ID NO:50).
(Lys Ile Ala Gly Lys Nva Ala)$_3$ (SEQ ID NO:51).
(His Ile Ala Gly His Ile Ala)$_3$ (SEQ ID NO:52).
(Ala Gly Lys Ile Ala Lys Ile)$_3$ (SEQ ID NO:53).
(Ile Ala Lys Ile Ala Gly Lys)$_3$ (SEQ ID NO:54).
(Lys Ile Ala Gly Arg Ile Ala)$_3$ (SEQ ID NO:55).
(Arg Ile Ala Gly Arg Ile Ala)$_3$ (SEQ ID NO:56).
(Lys Val Ala Gly Lys Ile Ala)$_3$ (SEQ ID NO:57).

(Lys Ile Ala Gly Lys Val Ala)$_3$ (SEQ ID NO:58).
(Ala Lys Ile Ala Gly Lys Ile)$_3$ (SEQ ID NO:59).
(Orn Ile Ala Gly Orn Ile Ala)$_3$ (SEQ ID NO:60).
(Lys Phe Ala Gly Lys Ile Ala)$_3$ (SEQ ID NO:61).
(Lys Ile Ala Gly Lys Phe Ala)$_3$ (SEQ ID NO:62).
(Lys Cha Ala Gly Lys Ile Ala)$_3$ (SEQ ID NO:63).
(Lys Nle Ala Lys Ile Ala Gly)$_3$ (SEQ ID NO:64).
(Arg Ile Ala Gly Lys Ile Ala)$_3$ (SEQ ID NO:65).
(Har Ile Ala Gly Har Ile Ala)$_3$ (SEQ ID NO:66).
(Xaa Ile Ala Gly Lys Ile Ala)$_3$ (SEQ ID NO:67).
(Lys Ile Ala Gly Xaa Ile Ala)$_3$ (SEQ ID NO:68).
Lys Ile Ala (Lys Ile Ala Gly Lys Ile Ala)$_3$(SEQ ID NO:69)

In (SEQ ID NO:67) and (SEQ ID NO:68), Xaa is p-aminophenylalanine.

In accordance with another embodiment, the amphiphilic peptide includes the following basic structure $X_{40}$:

$$R_{31}\text{-}R_{32}\text{-}R_{32}\text{-}R_{33}\text{-}R_{34}\text{-}R_{32}\text{-}R_{32}\text{-}R_{31}\text{-}R_{32}\text{-}R_{32}\text{-}R_{32}\text{-}R_{34}\text{-}R_{32}\text{-}R_{32},$$

wherein $R_{31}$, $R_{32}$, and $R_{33}$ are as hereinabove described, and $R_{34}$ is a basic hydrophilic or hydrophobic amino acid.

In accordance with one embodiment, the peptide may include the following structure:

$$Y_{40}\text{-}X_{40},$$

wherein $X_{40}$ is as hereinabove described, and $Y_{40}$ is:
(i) $R_{32}$;
(ii) $R_{32}\text{-}R_{32}$;
(iii) $R_{34}\text{-}R_{32}\text{-}R_{32}$;
(iv) $R_{33}\text{-}R_{34}\text{-}R_{32}\text{-}R_{32}$;
(v) $R_{32}\text{-}R_{33}\text{-}R_{34}\text{-}R_{32}\text{-}R_{32}$;
(v) $R_{32}\text{-}R_{32}\text{-}R_{33}\text{-}R_{34}\text{-}R_{32}\text{-}R_{32}$, or
(vii) $R_{31}\text{-}R_{32}\text{-}R_{32}\text{-}R_{33}\text{-}R_{34}\text{-}R_{32}\text{-}R_{32}$.

wherein $R_{31}$, $R_{32}$, $R_{33}$ and $R_{34}$ are as hereinabove described.

In accordance with another embodiment, the peptide may include the following structure:

$$X_{40}\text{-}Z_{40},$$

wherein $X_{40}$ is as hereinabove described and $Z_{40}$ is:
(i) $R_{31}$;
(ii) $R_{31}\text{-}R_{32}$;
(iii) $R_{31}\text{-}R_{32}\text{-}R_{32}$;
(iv) $R_{31}\text{-}R_{32}\text{-}R_{32}\text{-}R_{33}$;
(v) $R_{31}\text{-}R_{32}\text{-}R_{32}\text{-}R_{33}\text{-}R_{34}$;
(vi) $R_{31}\text{-}R_{32}\text{-}R_{32}\text{-}R_{33}\text{-}R_{34}\text{-}R_{32}$; or
(vii) $R_{31}\text{-}R_{32}\text{-}R_{32}\text{-}R_{33}\text{-}R_{34}\text{-}R_{32}\text{-}R_{32}$, wherein $R_{31}$, $R_{32}$, $R_{33}$, and $R_{34}$ are as hereinabove described.

In accordance with yet another embodiment the peptide may include the following structure:

$$(Y_{40})_a\text{-}X_{40}\text{-}(Z_{40})_b,$$

wherein $Y_{40}$ and $Z_{40}$ are as previously defined, a is 0 or 1, and b is 0 or 1. In a preferred embodiment, the peptide has the following structural formula as given in the accompanying sequence listing:

(SEQ ID NO:70)

In another preferred embodiment, the peptide has the following structural formula as given in the accompanying sequence listing:

(SEQ ID NO:71)

In accordance with a further embodiment, the peptide has one of the one of the following structural formulae as given in the accompanying sequence listing:

(SEQ ID NO:72)
(SEQ ID NO:73)
(SEQ ID NO:74)
(SEQ ID NO:75)
(SEQ ID NO:76)
(SEQ ID NO:77)
(SEQ ID NO:78)
(SEQ ID NO:79)
(SEQ ID NO:80)
(SEQ ID NO:81)
(SEQ ID NO:82)
(SEQ ID NO:83)
(SEQ ID NO:84)
(SEQ ID NO:85)
(SEQ ID NO:86)
(SEQ ID NO:87)

In accordance with another embodiment, the peptide may include the following structural formula:

-(Lys Ile Ala Lys Lys Ile Ala)-$_n$, wherein n is from 2 to 5. Preferably, n is 3, and the peptide has the following structural formula:

(Lys Ile Ala Lys Lys Ile Ala)$_3$(SEQ ID NO:88)

In accordance with another embodiment, the peptide may include the following structural formula:

-(Lys Phe Ala Lys Lys Phe Ala)-$_n$ wherein n is from 2 to 5.

Preferably, n is 3, and the peptide has the following structural formula:

(Lys Phe Ala Lys Lys Phe Ala)$_3$(SEQ ID NO:89)

In accordance with another embodiment, the peptide may include the following structural formula:

-(Lys Phe Ala Lys Lys Ile Ala)-$_n$ wherein n is from 2 to 5. Preferably n is 3, and the peptide has the following structural formula:

(Lys Phe Ala Lys Lys Ile Ala)$_3$(SEQ ID NO:90).

In accordance with another embodiment, the peptide may be selected from the group consisting of the following structural formulae as given in the accompanying sequence listing:

(SEQ ID NO:91)
(SEQ ID NO:92)
(SEQ ID NO:93)
(SEQ ID NO:94)

In accordance with yet another embodiment, the peptide may be a cecropin or sarcotoxin.

The term cecropins includes the basic structure as well as analogues and derivatives thereof. The cecropins and analogues and derivatives thereof are described in Ann. Rev. Microbiol. 1987, Vol. 41, pages 103–26, in particular page 108, and in Christensen, et al., PNAS Vol. 85, pgs. 5072–76, which are hereby incorporated by reference.

The term sarcotoxins includes the basic materials as well as analogues and derivatives thereof. The sarcotoxins and analogues and derivatives thereof are described in Molecular Entomology, pages 369–78, in particular page 375, Alan R. Liss, Inc. (1987), which is hereby incorporated by reference.

In another embodiment, the amphiphilic peptide includes the following basic structure $X_{50}$:

$$R_{41}\text{-}R_{42}\text{-}R_{42}\text{-}R_{41}\text{-}R_{42}\text{-}R_{42}\text{-}R_{41}\text{-}R_{41}\text{-}R_{42}\text{-}R_{41}\text{-}R_{41}.$$

$R_{41}$ is a hydrophobic amino acid, and $R_{42}$ is a basic hydrophilic or neutral hydrophilic amino acid.

In one embodiment, the peptide includes the basic structure $Y_{50}\text{-}X_{50}$ wherein $X_{50}$ is as hereinabove described and $Y_{50}$ is:

(i) $R_{41}$;
(ii) $R_{42}\text{-}R_{41}$; or
(iii) $R_{42}\text{-}R_{42}\text{-}R_{41}$, wherein $R_{41}$ and $R_{42}$ are as hereinabove described.

In one embodiment, $R_{41}$ is leucine. In another embodiment, $R_{42}$ is lysine. Representative examples of peptides in accordance with this aspect of the present invention include those having the following structures:

(SEQ ID NO: 95)
(SEQ ID NO: 96)
(SEQ ID NO: 97)
(SEQ ID NO: 98)

In accordance with another embodiment, the amphiphilic peptide includes the following basic structure $X_{52}$:

$$R_{42}\text{-}R_{41}\text{-}R_{42}\text{-}R_{42}\text{-}R_{41}\text{-}R_{41}\text{-}R_{42}\text{-}R_{42}\text{-}R_{41}\text{-}R_{42}\text{-}R_{42},$$

wherein $R_{41}$ is a hydrophobic amino acid and $R_{42}$ is a basic hydrophilic or neutral hydrophilic amino acid.

In one embodiment $R_{41}$ is leucine. In another embodiment, $R_{42}$ is lysine.

In one embodiment, the peptide includes the basic structure $Y_{52}\text{-}X_{52}$, wherein $X_{52}$ is as hereinabove described, and $Y_{52}$ is:

(i) $R_{42}$;
(ii) $R_{41}\text{-}R_{42}$;
(iii) $R_{41}\text{-}R_{41}\text{-}R_{42}$;
(iv) $R_{42}\text{-}R_{41}\text{-}R_{41}\text{-}R_{42}$; or
(v) $R_{42}\text{-}R_{42}\text{-}R_{41}\text{-}R_{41}\text{-}R_{42}$.

In one embodiment, the peptide may have the following structure;

Lys Lys Leu Leu Lys Lys Leu Lys Lys Leu    (SEQ ID NO: 99)
         5                10
Leu Lys Lys Leu Arg Arg
         15

In another embodiment, the peptide includes the basic structure $X_{52}\text{-}Z_{52}$, wherein $X_{52}$ is as hereinabove described, and $Z_{52}$ is:

(i) $R_{41}$;
(ii) $R_{41}\text{-}R_{41}$;
(iii) $R_{41}\text{-}R_{41}\text{-}R_{42}$;
(iv) $R_{41}\text{-}R_{41}\text{-}R_{42}\text{-}R_{42}$; or
(v) $R_{41}\text{-}R_{41}\text{-}R_{42}\text{-}R_{42}\text{-}R_{41}$;

In one embodiment, the peptide may have the following structure:

(SEQ ID NO: 100)
Lys Leu Lys Lys Leu Leu Lys Lys Leu Lys Lys Leu Leu Lys
         5                10
Lys Leu
15

In another embodiment, the peptide may include the structure:

$$(Y_{52})_a\text{-}X_{52}\text{-}(Z_{52})_b,$$

wherein $X_{52}$, $Y_{52}$ and $Z_{52}$ are as hereinabove described, and a is 0 or 1, and b is 0 or 1.

In accordance with another embodiment, the peptide includes the following basic structure $X_{54}$:

$$\text{-}R_{41}\text{-}R_{42}\text{-}R_{42}\text{-}R_{41}\text{-}R_{41}\text{-}R_{42}\text{-}R_{42}\text{-}R_{41}\text{-}R_{42}\text{-}R_{42}\text{-}R_{41}\text{-}R_{41}\text{-}R_{42}\text{-}R_{42}\text{-}R_{43}\text{-},$$

wherein $R_{41}$ and $R_{42}$ are as hereinabove described, and $R_{43}$ is a neutral hydrophilic amino acid.

In one embodiment, the peptide may have the following structure:

(SEQ ID NO:101)

In another embodiment, the peptide may have the following structure:

(SEQ ID NO:102)

In accordance with yet another embodiment, the peptide includes the following basic structure $X_{56}$:

$$R_{41}\text{-}R_{42}\text{-}R_{41}\text{-}R_{41}\text{-}R_{42}\text{-}R_{42}\text{-}R_{41}\text{-}R_{41}\text{-}R_{42}\text{-}R_{42}\text{-}R_{44},$$

wherein $R_{41}$ and $R_{42}$ are as hereinabove described, and $R_{44}$ is a neutral hydrophilic amino acid or proline.

In one embodiment, the peptide may include the following structure $Y_{56}\text{-}X_{56}$, wherein $X_{56}$ is the basic peptide structure hereinabove described, and $Y_{56}$ is:

(i) $\text{-}R_{41}$
(ii) $\text{-}R_{41}\text{-}R_{41}$;
(iii) $\text{-}R_{42}\text{-}R_{41}\text{-}R_{41}$;
(iv) $\text{-}R_{41}\text{-}R_{42}\text{-}R_{41}\text{-}R_{41}$;
(v) $\text{-}R_{41}\text{-}R_{41}\text{-}R_{42}\text{-}R_{41}\text{-}R_{41}$;
(vi) $\text{-}R_{42}\text{-}R_{41}\text{-}R_{41}\text{-}R_{42}\text{-}R_{41}\text{-}R_{41}$; or
(vii) $\text{-}R_{42}\text{-}R_{42}\text{-}R_{41}\text{-}R_{41}\text{-}R_{41}\text{-}R_{42}\text{-}R_{41}\text{-}R_{41}$, wherein $R_{41}$ and $R_{42}$ are as hereinabove described.

In one embodiment, the peptide may include the structure:

$$X_{56}\text{-}Z_{56},$$

wherein $X_{56}$ is as hereinabove described, and $Z_{56}$ is:

(i) $\text{-}R_{42}$;
(ii) $\text{-}R_{42}\text{-}R_{42}$;
(iii) $\text{-}R_{42}\text{-}R_{42}\text{-}R_{41}$;
(iv) $\text{-}R_{42}\text{-}R_{42}\text{-}R_{41}\text{-}R_{41}$;
(v) $\text{-}R_{42}\text{-}R_{42}\text{-}R_{41}\text{-}R_{41}\text{-}R_{42}$;
(vi) $\text{-}R_{42}\text{-}R_{42}\text{-}R_{41}\text{-}R_{41}\text{-}R_{42}\text{-}R_{42}$; or
(vii) $\text{-}R_{42}\text{-}R_{42}\text{-}R_{41}\text{-}R_{41}\text{-}R_{42}\text{-}R_{42}\text{-}R_{4}$.

In a preferred embodiment, the peptide may have one of the following structures:

(SEQ ID NO:103); or (SEQ ID NO:104).

In another embodiment, the peptide may have the structure $(Y_{56})_a\text{-}X_{56}\text{-}(Z_{56})_b$, wherein $X_{56}$, $Y_{56}$, and $Z_{56}$ are as hereinabove described, a is 0 or 1, and b is 0 or 1.

In accordance with another embodiment, the peptide includes the following basic structure $X_{58}$:

$R_{41}\text{-}R_{41}\text{-}R_{42}\text{-}R_{42}\text{-}R_{41}\text{-}R_{42}\text{-}R_{42}\text{-}R_{41}\text{-}R_{41}\text{-}R_{42}\text{-}R_{42}\text{-}R_{41}\text{-}R_{43}$, wherein $R_{41}$, $R_{42}$ and $R_{43}$ are as hereinabove described.

In accordance with another embodiment, the peptide may include the structure $Y_{58}\text{-}X_{58}$, wherein $X_{58}$ is as hereinabove described, and $Y_{58}$ is:

(i) $-R_4$;
(ii) $-R_{42}\text{-}R_{41}$;
(iii) $-R_{42}\text{-}R_{42}\text{-}R_{41}$;
(iv) $-R_{41}\text{-}R_{42}\text{-}R_{42}\text{-}R_{41}$;
(v) $-R_{41}\text{-}R_{41}\text{-}R_{42}\text{-}R_{42}\text{-}R_{41}$;
(vi) $-R_{42}\text{-}R_{41}\text{-}R_{41}\text{-}R_{42}\text{-}R_{42}\text{-}R_{41}$; or
(vii) $-R_{42}\text{-}R_{42}\text{-}R_{41}\text{-}R_{41}\text{-}R_{42}\text{-}R_{42}\text{-}R_{41}$, wherein $R_{41}$ and $R_{42}$ are as hereinabove described.

In another embodiment, the peptide includes the structure $X_{58}\text{-}Z_{58}$, wherein $X_{58}$ is as hereinabove described, and $Z_{58}$ is:

(i) $-R_{41}$;
(ii) $-R_{41}\text{-}R_{45}$;
(iii) $-R_{41}\text{-}R_{45}\text{-}R_{45}$;
(iv) $-R_{41}\text{-}R_{45}\text{-}R_{45}\text{-}R_{43}$;
(v) $-R_{41}\text{-}R_{45}\text{-}R_{45}\text{-}R_{43}\text{-}R_{41}$;
(vi) $-R_{41}\text{-}R_{45}\text{-}R_{45}\text{-}R_{43}\text{-}R_{41}\text{-}R_{43}$;
(vii) $-R_{41}\text{-}R_{45}\text{-}R_{45}\text{-}R_{43}\text{-}R_{41}\text{-}R_{43}\text{-}R_{43}$,
(viii) $-R_{41}\text{-}R_{45}\text{-}R_{45}\text{-}R_{43}\text{-}R_{41}\text{-}R_{43}\text{-}R_{43}\text{-}R_{45}$; or
(ix) $-R_{41}\text{-}R_{45}\text{-}R_{45}\text{-}R_{43}\text{-}R_{41}\text{-}R_{43}\text{-}R_{43}\text{-}R_{45}\text{-}R_{43}$, wherein $R_{41}$ and $R_{43}$ are as hereinabove described, and $R_{45}$ is proline.

In one embodiment, the peptide has the following structure:

(SEQ ID NO:105).

In one embodiment, the peptide may have the structure $(Y_{58})_a\text{-}X_{58}\text{-}(Z_{58})_b$, wherein $X_{58}$, $Y_{58}$, and $Z_{58}$ are as hereinabove described, a is 0 or 1, and b is 0 or 1.

In accordance with another embodiment, the peptide includes the following basic structure $X_{60}$;

$R_{41}-R_{41}-R_{43}-R_{42}-R_{41}-R_{41}-R_{41}-R_{41}-R_{41}-R_{41}-R_{42}-R_{41}-R_{41}-R_{42}-R_{42}-R_{41}-R_{41}-R_{42}-R_{42}-R_{42}-R_{41}$, wherein $R_{41}$, $R_{42}$, and $R_{43}$ are as hereinabove described. In one embodiment, the peptide may have the following structure:

(SEQ ID NO:106).

In another embodiment, the peptide may include the structure $X_{60}\text{-}Z_{60}$, wherein $X_{60}$ is as hereinabove described, and $Z_{60}$ is:

(i) $-R_{42}$;
(ii) $-R_{42}\text{-}R_{42}$;
(iii) $-R_{42}\text{-}R_{42}\text{-}R_{41}$;
(iv) $-R_{42}\text{-}R_{42}\text{-}R_{41}\text{-}R_{41}$;
(v) $-R_{42}\text{-}R_{42}\text{-}R_{41}\text{-}R_{41}\text{-}R_{42}$;
(vi) $-R_{42}\text{-}R_{42}\text{-}R_{41}\text{-}R_{41}\text{-}R_{42}\text{-}R_{42}$; or
(vii) $-R_{42}\text{-}R_{42}\text{-}R_{41}\text{-}R_{41}\text{-}R_{42}\text{-}R_{42}\text{-}R_{41}$.

In accordance with yet another embodiment, the peptide has a structure selected from the group consisting of:

(a) $R_{41}\text{-}R_{42}\text{-}R_{42}\text{-}R_{41}\text{-}R_{42}\text{-}R_{42}\text{-}R_{41}$;
(b) $R_{41}\text{-}R_{41}\text{-}R_{42}\text{-}R_{42}\text{-}R_{41}\text{-}R_{42}\text{-}R_{42}\text{-}R_{41}$;
(c) $R_{42}\text{-}R_{41}\text{-}R_{41}\text{-}R_{42}\text{-}R_{42}\text{-}R_{41}\text{-}R_{42}\text{-}R_{42}\text{-}R_{41}$;
(d) $R_{42}\text{-}R_{42}\text{-}R_{41}\text{-}R_{41}\text{-}R_{42}\text{-}R_{42}\text{-}R_4\text{-}R_{42}\text{-}R_{42}\text{-}R_{41}$; and
(e) $R_{41}\text{-}R_{42}\text{-}R_{42}\text{-}R_{41}\text{-}R_{41}\text{-}R_{42}\text{-}R_{42}\text{-}R_{41}\text{-}R_{42}\text{-}R_{42}\text{-}R_{41}$, wherein $R_{41}$ and $R_{42}$ are as hereinabove described.

In one embodiment, the peptide has the structure (a), and a representative example of such a structure is (SEQ ID NO:107), which is given in the accompanying sequence listing.

In another embodiment, the peptide has the structure (b), and a representative example of such a structure is (SEQ ID NO:108), which is given In the accompanying sequence listing.

In another embodiment, the peptide has the structure (c), and a representative example of such a structure is (SEQ ID NO:109) as given the accompanying sequence listing.

In yet another embodiment, the peptide has the structure (d), and a representative example of such a structure is (SEQ ID NO:110) as given in the accompanying sequence listing.

In a further embodiment, the peptide has the structure (e), and representative examples of such a structure are (SEQ ID NO:111) and (SEQ ID NO:112) as given in the accompanying sequence listing.

In accordance with another embodiment, the peptide has the following structural formula:

(SEQ ID NO:113).

In accordance with another embodiment, the peptide is melittin.

Melittin is an amphipathic peptide consisting of 26 amino acid residues, and is isolated from honeybee (Apis mellifera) venom. The peptide is known to be cytolytic. See Habermann, et al., *Hoppe-Seyler's Zeitschrift Physiol. Chem.*, Vol. 348, pgs. 37–50 (1987). Melittin has the following structural formula as represented by the three-letter amino acid code:

| Gly | Ile | Gly | Ala | Val | Leu | Lys | Val | Leu | (SEQ ID NO: 114) |
|-----|-----|-----|-----|-----|-----|-----|-----|-----|-----|
|     |     |     |     | 5   |     |     |     |     |     |
| Thr | Thr | Gly | Leu | Pro | Ala | Leu | Ile | Ser |     |
| 10  |     |     |     |     | 15  |     |     |     |     |
| Trp | Ile | Lys | Arg | Lys | Arg | Gln | Gln |     |     |
|     | 20  |     |     |     |     | 25  |     |     |     |

In another embodiment, the peptide purified in accordance with the present invention is an apidaecin. The term apidaecin as used herein includes the basic structure as well as analogues and derivaties thereof. Apidaecins are further described in European Patent Application No. 299,828.

In accordance with yet another embodiment, the amphiphilic peptide or protein may be an ion channel-forming peptide or protein.

Ion channel-forming proteins or peptides which may be employed include defensins, also known as human neutrophil antimicrobial peptides (HNP), major basic protein (MBP) of eosinophils, bactericidal permeability-increasing protein (BPI), and a pore-forming cytotoxin called variously perforin, cytolysin, or pore-forming protein. Defensins are described in Selsted, et al., *J. Clin. Invest.*, Vol. 76, pgs. 1436–1439 (1985). MBP proteins are described in Wasmoen, et al., *J. Biol. Chem.*, Vol. 263, pgs 12559–12563. (1988). BPI proteins are described in Ooi, et al, *J. Biol. Chem.*, Vol. 262, pgs. 14891–14894 (1987). Perforin is described in Henkart, et al., *J. Exp. Med.*, 160: 75 (1984), and in Podack, et al., *J. Exp. Med.*, 160:695 (1984). The above articles ere hereby incorporated by reference.

The term ion channel-forming proteins includes the basic structures of the ion channel-forming proteins as well as analogues and derivatives.

In accordance with yet another embodiment, each of the amino acid residues of the peptide may be a D-amino acid or glycine.

The peptides may be produced by known techniques and obtained in substantially pure form. For example, the peptides may be synthesized on an automatic peptide synthesizer. *Journal of the American Chemical Society*, Vol. 85, pgs. 2149–54 (1963). It is also possible to produce such peptides by genetic engineering techniques. The codons encoding the amino acids are known to those skilled in the art, and thus one may construct DNA encoding any of the peptides by accepted techniques, and clone such DNA into an expression vehicle such as, for example, a plasmid, and transfect such an expression vehicle into a cell which will express the peptide. Thus, it is contemplated within the scope of the present invention that one may treat a gynecological malignancy by administering transfected cells which include an expression vehicle to a host containing DNA encoding ion channel-forming peptide(s) or protein(s) such as those hereinabove described.

It is also to be understood that the peptides or proteins may be administered in combination with one another.

In accordance with another embodiment, the peptide or protein may be administered in combination with an ion having pharmacological properties.

An ion having pharmacological properties is one which when introduced into a gynecologically malignant cell, inhibits and/or prevents and/or destroys the growth of the gynecologically malignant cell.

Such an ion having pharmacological properties is one which in the absence of an ion channel-forming peptide or protein is unable to cross a natural or synthetic membrane; in particular a cell membrane, in sufficient amounts to affect a cell adversely.

The peptide or protein and ion having pharmacological properties may be administered as a single composition or in separate compositions, and the single or separate compositions may include additional materials, active and/or inactive, in addition to the peptide or protein and ion having pharmacological properties. As representative examples of ions having pharmacological properties which may be employed, there may be mentioned fluoride, peroxide, bicarbonate, silver, zinc, mercury, arsenic, copper, platinum, antimony, gold, thallium, nickel, selenium, bismuth, and cadmium ions.

The peptide or protein and ion having pharmacological properties, whether administered or prepared in a single composition or in separate compositions, are employed in amounts effective to inhibit and/or prevent and/or destroy the growth of the gynecological malignancy. In effect, the ion potentiates the action of the peptide, i.e., the amount of the ion is effective to reduce the maximum effective concentration of the peptide or protein for inhibiting growth of a gynecological malignancy.

The ion having pharmacological properties, when used systemically (e.g., intravenously, intraperitoneally, intralesionally), is generally employed in an amount of from 1 mg to 10 mg per kg of host weight. Peptide or protein dosages may be within the ranges hereinabove described.

The ion may be administered in the form of a salt such as, for example, sodium fluoride.

The peptides or proteins may be administered combination with chemotherapeutic agents such as, but not limited to, cyclophosphamide, cisplatin, doxorubicin, hexamethylamine and VP-16.

The peptides or proteins may be administered before, during, or after radiation treatment, chemotherapy, or surgery. The administration of the peptides or proteins during surgery or radiation treatment may be advantageous in inhibiting, preventing, and/or destroying potential "loose" malignant cells capable of colonizing other sites.

The invention will now be described with respect to the following examples; however, the scope of the present invention is not intended to be limited thereby.

EXAMPLE 1

Groups of mice, with six mice in each group, were injected with murine Spontaneous Ovarian Teratoma cells (SOT cells). At day 2, or at day 2 and day 5 after injection, the mice were injected with a saline solution, 5 mg/kg adriamycin (day 2 only), with 22 mg/kg of a peptide having the structure (SEQ ID NO:115)-$NH_2$, or, in which each amino acid residue of (SEQ ID NO:115)-$NH_2$ is a D-amino acid residue, such peptide hereinafter referred to as D-(SEQ ID NO:115)-$NH_2$ or with $_{130}$ mg/kg of Cecropin A (SEQ ID NO:116)-$NH_2$. The animals were monitored for survival time, the number of survivors in each group, the increase in lifespan, and the increase in body weight. As shown in FIG. 1, body weight data shows that the accumulation of ascites fluid was delayed at least 20 days in mice treated with D-(SEQ ID NO:115)-$NH_2$ or (SEQ ID NO:116)-$NH_2$ or adriamycin whereas untreated mice began to accumulate fluid 5 to 7 days after tumor cells were implanted.

Figure 2:
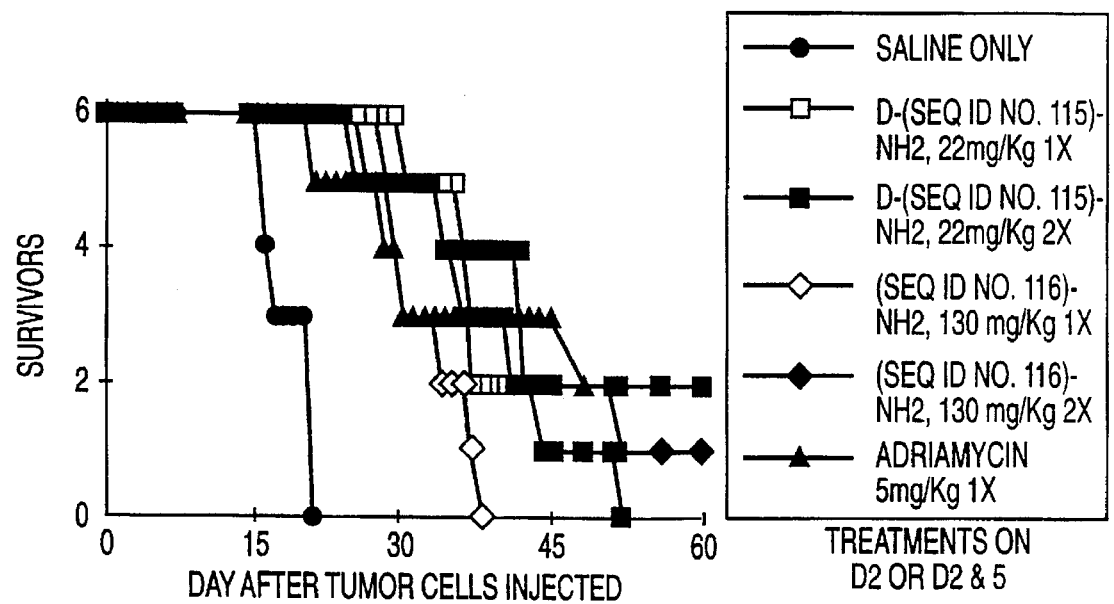

As shown in FIG. 2, the untreated mice succumbed to the tumor burden within 20 days while all of the treated mice lived more than 70% longer. Using the median day of death for the group (3 animals dead) as an endpoint, the increase in lifespan produced by D-(SEQ ID NO:115)-$NH_2$ was 115% (administered on day 2 only), and 144% (administered on day 2 and day 5). The increase in lifespan produced by (SEQ ID NO:116)-$NH_2$ was 100% (administered on day 2), and 112% (administered on day 2 and day 5). The treatment with adriamycin increased the lifespan by 76%.

EXAMPLE 2

Groups of mice, with 5 or 6 mice in each group, were injected with Spontaneous Ovarian Teratoma Cells. At 2 days and 5 days after the injection of the Spontaneous Ovarian Teratoma Cells (SOT cells), the groups of mice were injected intraperitoneally with a control saline solution, adriamycin, or with one of the following peptides:

(SEQ ID NO:7)-$NH_2$ (SEQ ID NO:117)-$NH_2$

D-(SEQ ID NO:117)-NH$_2$
(SEQ ID NO:115)-NH$_2$
D-(SEQ ID NO:115)-NH$_2$
(SEQ ID NO:116)-NH$_2$
Octanoyl-(SEQ ID NO:27)-NH$_2$ The mice in each group were then monitored for median survival time (in days) and for increase in life span (ILS) vis a vis the control group. The median survival time is the day of death of the third mouse in each group. The results for the groups of mice given intraperitoneal injections of peptide at days 2 and 5 following injection of SOT cells are given in Table I below.

TABLE I

| Peptide | Dose (mg/kg/day) | Median Survival Time (controls) | ILS |
| --- | --- | --- | --- |
| Control | 0 | 17, 21, 21 | — |
| (SEQ ID NO:7)-NH$_2$ | 60/50 | >42(21) | 100% |
| (SEQ ID NO:117)-NH$_2$ | 45 | 38(21) | 83% |
| D-(SEQ ID NO:117)-NH$_2$ | 15 | 35(21) | 67% |
| (SEQ ID NO:11.5)-NH$_2$ | 22 | 38(21) | 81% |
| (SEQ ID NO:115)-NH$_2$ | 20 | 42(21) | 100% |
| D-(SEQ ID NO:115)-NH$_2$ | 22 | 41.5(17) | 144% |
| D-(SEQ ID NO:115)-NH$_2$ | 22 | 32(21) | 52% |
| (SEQ ID NO:116)-NH$_2$ | 130 | 36 | 112% |
| Oct-(SEQ ID NO:27)-NH$_2$ | 20 | 42(21) | 100% |

EXAMPLE 3

Figure 3:
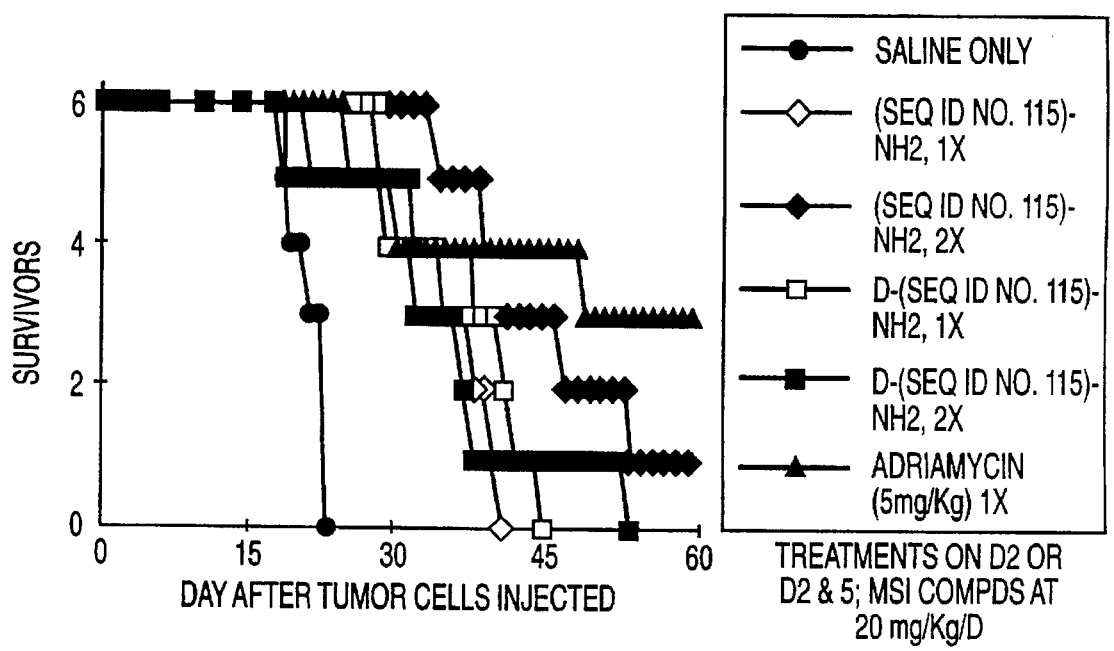
Figure 4:
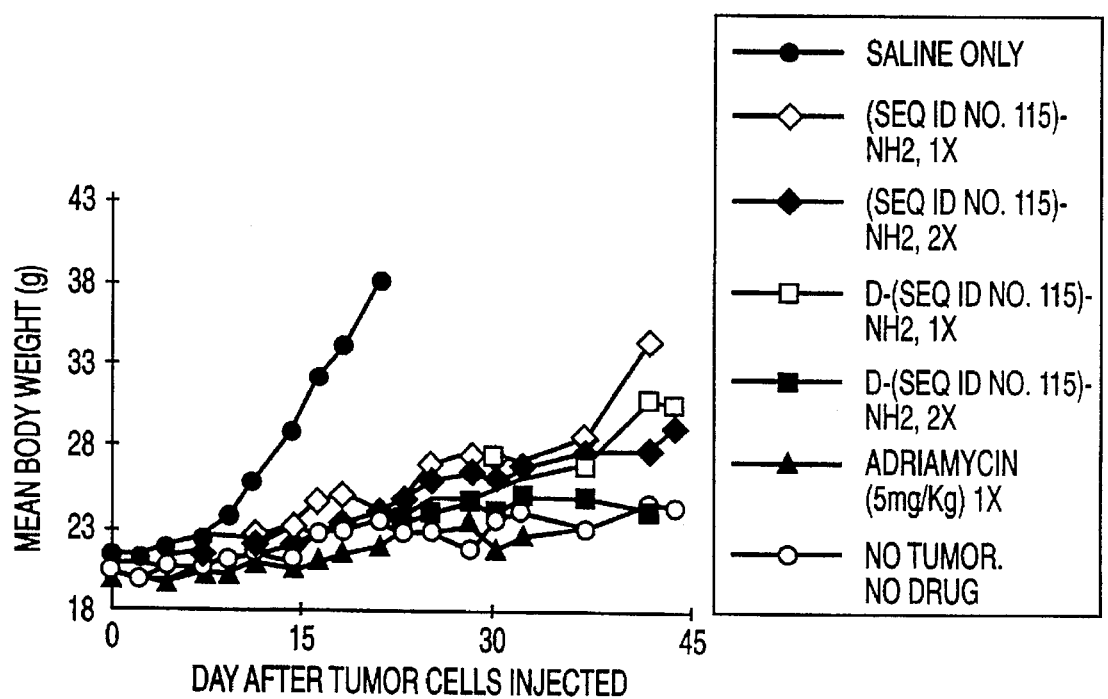

Groups of mice, with 6 mice in each group, were injected with Spontaneous Ovarian Teratoma Cells as described in Example 2. At 2 days, or at 2 days and 5 days after the injection of the SOT cells, the groups of mice were injected with saline (control), adriamycin (5 mg/kg-on day 2 only), or with 20 mg/kg of (SEQ ID NO:115)-NH$_2$ or D-(SEQ ID NO:115)-NH$_2$. The mice were then monitored for survival time, as well as for body weight. As shown in FIG. 3, those mice treated with (SEQ ID NO:115)-NH$_2$ or D-(SEQ ID NO:115)-NH$_2$ had significantly greater survival times and had more survivors than those of the control group. As shown in FIG. 4, the body weight data indicates that the accumulation of ascites fluid in mice treated with (SEQ ID NO:115)-NH$_2$, D-(SEQ ID NO:115)-NH$_2$, or adriamycin was delayed and was also significantly less vis a vis the control group.

It is to be understood, however, that the scope of the present invention is not to be limited to the specific embodiments described above. The invention may be practiced other than as particularly described and still be within the scope of the accompanying claims.

---

What is claimed is:

1. A process for inhibiting the growth of ovarian cancer cells in a mammalian host, comprising:

administering at least one biologically active magainin peptide in an amount sufficient to inhibit the growth of ovarian cancer cells.

2. The process of claim 1 wherein the magainin peptide is selected from the group consisting of SEQ ID NO 7, SEQ ID NO 115, and SEQ ID NO 117.

3. The process of claim 2 wherein the magainin peptide is comprised of D amino acids.

4. A process for inhibiting the growth of ovarian cancer cells in a mammalian host, comprising:

administering at least one biologically active amphiphilic ion channel-forming peptide selected from the group consisting of SEQ ID NO 116 and SEQ ID NO 27 in an amount sufficient to inhibit the growth of ovarian cancer cells.

5. The process of claim 4 wherein the SEQ ID NO 27 is administered as Octanoyl-(SEQ ID NO 27)-NH$_2$.

6. The process of claim 1 wherein the magainin peptide is administered intralesionally.

\* \* \* \* \*